US012685448B2

(12) United States Patent
Schwartz et al.

(10) Patent No.: US 12,685,448 B2
(45) Date of Patent: Jul. 21, 2026

(54) CONTROLLED FLOW INFUSION MICROVASCULAR DYSFUNCTION DIAGNOSTIC AND THERAPY

(71) Applicant: CorFlow Therapeutics AG, Baar (CH)

(72) Inventors: Robert S. Schwartz, Inver Grover Heights, MN (US); Jon Helge Hoem, Baar (CH); Sabrina Frey, Bern (CH); Oliver Bludau, Baar (CH)

(73) Assignee: CorFlow Therapeutics AG, Baar (CH)

( * ) Notice: Subject to any disclaimer, the term of this patent is extended or adjusted under 35 U.S.C. 154(b) by 181 days.

(21) Appl. No.: 17/327,433

(22) Filed: May 21, 2021

(65) Prior Publication Data
US 2021/0361170 A1     Nov. 25, 2021

Related U.S. Application Data

(60) Provisional application No. 63/029,152, filed on May 22, 2020.

(51) Int. Cl.
| | |
|---|---|
| *A61B 5/021* | (2006.01) |
| *A61B 5/00* | (2006.01) |
| *A61B 5/026* | (2006.01) |

(52) U.S. Cl.
CPC .............. *A61B 5/021* (2013.01); *A61B 5/026* (2013.01); *A61B 5/4839* (2013.01);
(Continued)

(58) Field of Classification Search
CPC ....... A61B 5/021; A61B 5/026; A61B 5/4839; A61B 5/6852; A61B 5/742; A61B 2562/0247; A61B 5/02152; A61B 5/02007; A61B 5/6853; A61B 5/0002; A61B 5/0215; A61B 5/02158; A61M 5/142;
(Continued)

(56) References Cited

U.S. PATENT DOCUMENTS

| | | |
|---|---|---|
| 4,689,041 A | 8/1987 | Corday et al. |
| 4,722,348 A | 2/1988 | Ligtenberg et al. |

(Continued)

FOREIGN PATENT DOCUMENTS

| | | |
|---|---|---|
| AU | 2017205404 A1 | 7/2018 |
| CA | 3010447 A1 | 7/2017 |

(Continued)

OTHER PUBLICATIONS

Costa, et al., "Mimicking Arterial Thrombosis in a 3d-printed Microfluidic in Vitro Vascular Model Based on Computed Tomography Angiography Data," Lab on a Chip, Royal Society of Chemistry, 17(16):2785-2792 (Jun. 2017).
(Continued)

*Primary Examiner* — Brian L Casler

(57) ABSTRACT
Methods and systems are provided for diagnosis and/or treatment of microvascular dysfunction, such as microvascular obstruction (MVO), in which the effects of collateral flow around a treatment site are addressed by injecting volumetric flows into a vessel using an infusion system to prevent or render negligible the collateral flow. Arterial pressures and fluidic flow rates sufficient to negate the collateral flow may be used to indicate the presence and/or severity of MVO for diagnostic and/or therapeutic purposes.

37 Claims, 12 Drawing Sheets

(52) U.S. Cl.
CPC ............ *A61B 5/6852* (2013.01); *A61B 5/742*
(2013.01); *A61B 2562/0247* (2013.01)

(58) Field of Classification Search
CPC ........ A61M 5/172; A61M 2005/16863; A61M
2205/50; A61M 2205/3334; A61M
2205/3331; A61M 2005/14208; A61M
2205/3344; A61M 5/16854; G16H 50/20;
G16H 40/67; G16H 40/63; G16H 20/17
USPC ...................................................... 600/485
See application file for complete search history.

(56) References Cited

U.S. PATENT DOCUMENTS

| | | | |
|---|---|---|---|
| 4,938,961 A | 7/1990 | Collins et al. |
| 4,961,738 A | 10/1990 | Mackin |
| 5,021,045 A | 6/1991 | Buckberg et al. |
| 5,082,025 A | 1/1992 | DeVries et al. |
| 5,108,365 A | 4/1992 | Woods, Jr. |
| 5,182,106 A | 1/1993 | Mezrow et al. |
| 5,197,485 A | 3/1993 | Grooters |
| 5,308,320 A | 5/1994 | Safar et al. |
| 5,324,260 A | 6/1994 | O'Neill et al. |
| 5,358,481 A | 10/1994 | Todd et al. |
| 5,370,989 A | 12/1994 | Stern et al. |
| 5,374,624 A | 12/1994 | Segel |
| 5,383,854 A | 1/1995 | Safar et al. |
| 5,423,745 A | 6/1995 | Todd et al. |
| 5,428,039 A | 6/1995 | Cohen |
| 5,462,524 A | 10/1995 | Powell et al. |
| 5,505,698 A | 4/1996 | Booth et al. |
| 5,552,267 A | 9/1996 | Stern et al. |
| 5,554,497 A | 9/1996 | Raymond |
| 5,558,644 A | 9/1996 | Boyd et al. |
| 5,643,921 A | 7/1997 | Grover |
| 5,648,071 A | 7/1997 | Hunter et al. |
| 5,662,607 A | 9/1997 | Booth et al. |
| 5,670,545 A | 9/1997 | Horwitz |
| 5,693,462 A | 12/1997 | Raymond |
| 5,699,793 A | 12/1997 | Brasile |
| 5,701,905 A | 12/1997 | Esch |
| 5,702,368 A | 12/1997 | Stevens et al. |
| 5,716,378 A | 2/1998 | Minten |
| 5,728,064 A | 3/1998 | Burns et al. |
| 5,738,096 A | 4/1998 | Ben-Haim |
| 5,738,649 A | 4/1998 | Macoviak |
| 5,738,652 A | 4/1998 | Boyd et al. |
| 5,755,687 A | 5/1998 | Donlon |
| 5,765,568 A | 6/1998 | Sweezer, Jr. et al. |
| 5,766,151 A | 6/1998 | Valley et al. |
| 5,769,812 A | 6/1998 | Stevens et al. |
| 5,792,094 A | 8/1998 | Stevens et al. |
| 5,795,325 A | 8/1998 | Valley et al. |
| 5,799,661 A | 9/1998 | Boyd et al. |
| 5,800,375 A | 9/1998 | Sweezer et al. |
| 5,810,757 A | 9/1998 | Sweezer, Jr. et al. |
| 5,814,016 A | 9/1998 | Valley et al. |
| 5,820,586 A | 10/1998 | Booth et al. |
| 5,820,593 A | 10/1998 | Safar et al. |
| 5,863,366 A | 1/1999 | Snow |
| 5,868,702 A | 2/1999 | Stevens et al. |
| 5,868,703 A | 2/1999 | Bertolero et al. |
| 5,879,316 A | 3/1999 | Safar et al. |
| 5,879,499 A | 3/1999 | Corvi |
| 5,885,238 A | 3/1999 | Stevens et al. |
| 5,906,588 A | 5/1999 | Safar et al. |
| 5,913,842 A | 6/1999 | Boyd et al. |
| 5,935,103 A | 8/1999 | Hill |
| 5,941,894 A | 8/1999 | Hill |
| 5,997,505 A | 12/1999 | Hill |
| 6,024,698 A | 2/2000 | Brasile |
| 6,029,671 A | 2/2000 | Stevens et al. |
| 6,043,273 A | 3/2000 | Duhaylongsod |
| 6,046,046 A | 4/2000 | Hassanein |
| 6,056,723 A | 5/2000 | Donlon |
| 6,060,454 A | 5/2000 | Duhaylongsod |
| 6,066,094 A | 5/2000 | Ben-Haim |
| 6,087,394 A | 7/2000 | Duhaylongsod |
| 6,090,096 A | 7/2000 | St. Goar et al. |
| 6,101,412 A | 8/2000 | Duhaylongsod |
| 6,110,139 A | 8/2000 | Loubser |
| 6,110,145 A | 8/2000 | Macoviak |
| 6,127,410 A | 10/2000 | Duhaylongsod |
| 6,132,397 A | 10/2000 | Davis et al. |
| 6,139,517 A | 10/2000 | Macoviak et al. |
| 6,156,005 A | 12/2000 | Theron |
| 6,165,162 A | 12/2000 | Safar et al. |
| 6,194,137 B1 | 2/2001 | Khirabadi et al. |
| 6,210,363 B1 | 4/2001 | Esch et al. |
| 6,248,086 B1 | 6/2001 | Sweezer et al. |
| 6,251,093 B1 | 6/2001 | Valley et al. |
| 6,254,563 B1 | 7/2001 | Macoviak et al. |
| 6,267,747 B1 | 7/2001 | Samson et al. |
| 6,285,898 B1 | 9/2001 | Ben-Haim |
| 6,293,920 B1 | 9/2001 | Sweezer et al. |
| 6,295,990 B1 | 10/2001 | Lewis et al. |
| 6,316,403 B1 | 11/2001 | Pinsky et al. |
| 6,321,909 B1 | 11/2001 | Wicomb et al. |
| 6,354,999 B1 | 3/2002 | Dgany et al. |
| 6,361,545 B1 | 3/2002 | Macoviak et al. |
| 6,371,935 B1 | 4/2002 | Macoviak et al. |
| 6,398,752 B1 | 6/2002 | Sweezer, Jr. et al. |
| 6,414,018 B1 | 7/2002 | Duhaylongsod |
| 6,423,031 B1 | 7/2002 | Donlon |
| 6,423,032 B2 | 7/2002 | Parodi |
| 6,426,362 B1 | 7/2002 | Miller et al. |
| 6,447,443 B1 | 9/2002 | Keogh et al. |
| 6,451,004 B1 | 9/2002 | Peters |
| 6,475,186 B1 | 11/2002 | Safar et al. |
| 6,482,171 B1 | 11/2002 | Corvi et al. |
| 6,485,450 B1 | 11/2002 | Owen |
| 6,485,500 B1 | 11/2002 | Kokish et al. |
| 6,488,671 B1 | 12/2002 | Constantz et al. |
| 6,491,039 B1 | 12/2002 | Dobak, III |
| 6,495,532 B1 | 12/2002 | Bathurst et al. |
| 6,508,777 B1 | 1/2003 | Macoviak et al. |
| 6,524,339 B1 | 2/2003 | Adams |
| 6,528,042 B1 | 3/2003 | Brown et al. |
| 6,540,781 B2 | 4/2003 | Adams |
| 6,547,760 B1 | 4/2003 | Samson et al. |
| 6,564,805 B2 | 5/2003 | Garrison et al. |
| 6,567,679 B1 | 5/2003 | Khuri et al. |
| 6,569,145 B1 | 5/2003 | Shmulewitz et al. |
| 6,572,638 B1 | 6/2003 | Dae et al. |
| RE38,203 E | 7/2003 | Kelly |
| 6,600,941 B1 | 7/2003 | Khuri |
| 6,602,276 B2 | 8/2003 | Dobak, III et al. |
| 6,613,069 B2 | 9/2003 | Boyd et al. |
| 6,645,197 B2 | 11/2003 | Garrison et al. |
| 6,669,680 B1 | 12/2003 | Macoviak et al. |
| 6,673,040 B1 | 1/2004 | Samson et al. |
| 6,673,041 B1 | 1/2004 | Macoviak |
| 6,673,042 B1 | 1/2004 | Samson et al. |
| 6,677,150 B2 | 1/2004 | Alford et al. |
| 6,685,732 B2 | 2/2004 | Kramer |
| 6,695,811 B2 | 2/2004 | Samson et al. |
| 6,695,864 B2 | 2/2004 | Macoviak et al. |
| 6,702,773 B1 | 3/2004 | Macoviak et al. |
| 6,711,436 B1 | 3/2004 | Duhaylongsod |
| 6,726,651 B1 | 4/2004 | Robinson et al. |
| 6,740,029 B2 | 5/2004 | Rogers et al. |
| 6,740,484 B1 | 5/2004 | Khirabadi et al. |
| 6,751,492 B2 | 6/2004 | Ben-Haim |
| 6,786,218 B2 | 9/2004 | Dobak, III |
| 6,794,124 B2 | 9/2004 | Steen |
| 6,811,551 B2 | 11/2004 | Dae et al. |
| 6,821,265 B1 | 11/2004 | Bertolero et al. |
| 6,835,188 B2 | 12/2004 | Samson et al. |
| 6,902,545 B2 | 6/2005 | Bertolero et al. |
| 6,902,556 B2 | 6/2005 | Grimes et al. |
| 6,905,494 B2 | 6/2005 | Yon et al. |
| 6,913,600 B2 | 7/2005 | Valley et al. |
| 6,915,149 B2 | 7/2005 | Ben-Haim |

(56)                    References Cited

U.S. PATENT DOCUMENTS

| | | | |
|---|---|---|---|
| 6,949,528 B1 | 9/2005 | Goddard et al. | |
| 6,949,529 B2 | 9/2005 | Bathurst et al. | |
| 6,953,655 B1 | 10/2005 | Hassanein et al. | |
| 6,983,179 B2 | 1/2006 | Ben-Haim | |
| 6,994,700 B2 | 2/2006 | Elkins et al. | |
| 7,001,378 B2 | 2/2006 | Yon et al. | |
| 7,017,581 B2 | 3/2006 | Boyd et al. | |
| 7,063,679 B2 | 6/2006 | Maguire et al. | |
| 7,104,981 B2 | 9/2006 | Elkins et al. | |
| 7,157,222 B2 | 1/2007 | Khirabadi et al. | |
| 7,176,015 B2 | 2/2007 | Alford et al. | |
| 7,238,360 B2 | 7/2007 | Shirwan | |
| 7,241,273 B2 | 7/2007 | Maguire et al. | |
| 7,259,273 B1 | 8/2007 | Goddard et al. | |
| 7,288,089 B2 | 10/2007 | Yon et al. | |
| 7,291,144 B2 | 11/2007 | Dobak, III et al. | |
| 7,338,434 B1 | 3/2008 | Haarstad et al. | |
| 7,364,566 B2 | 4/2008 | Elkins et al. | |
| 7,371,254 B2 | 5/2008 | Dobak, III | |
| 7,399,272 B2 | 7/2008 | Kim et al. | |
| 7,449,018 B2 | 11/2008 | Kramer | |
| 7,494,460 B2 | 2/2009 | Haarstad et al. | |
| 7,507,235 B2 | 3/2009 | Keogh et al. | |
| 7,510,569 B2 | 3/2009 | Dae et al. | |
| 7,563,247 B2 | 7/2009 | Maguire et al. | |
| 7,572,217 B1 * | 8/2009 | Koenig | A61M 60/152 |
| | | | 600/16 |
| 7,585,836 B2 | 9/2009 | Goodson, IV et al. | |
| 7,615,548 B2 | 11/2009 | Gottlieb et al. | |
| 7,686,781 B2 | 3/2010 | Vinten-Johansen | |
| 7,722,596 B2 | 5/2010 | Shapland et al. | |
| 7,758,890 B2 | 7/2010 | Anderson et al. | |
| 7,766,961 B2 | 8/2010 | Patel et al. | |
| 7,775,988 B2 | 8/2010 | Pijls | |
| 7,837,650 B1 | 11/2010 | Cox et al. | |
| 7,914,503 B2 | 3/2011 | Goodson, IV et al. | |
| 7,951,183 B2 | 5/2011 | Dobak, III | |
| 7,993,325 B2 | 8/2011 | Elkins et al. | |
| 8,043,283 B2 | 10/2011 | Dobak, III et al. | |
| 8,043,351 B2 | 10/2011 | Yon et al. | |
| 8,067,150 B2 | 11/2011 | Mangino | |
| 8,075,490 B2 | 12/2011 | Charlez | |
| 8,076,096 B2 | 12/2011 | Shirwan | |
| 8,100,123 B2 | 1/2012 | Belson | |
| 8,110,225 B2 | 2/2012 | Anderson et al. | |
| 8,128,963 B2 | 3/2012 | Pinsky et al. | |
| 8,157,794 B2 | 4/2012 | Dobak, III et al. | |
| 8,163,000 B2 | 4/2012 | Dobak, III et al. | |
| 8,177,704 B1 | 5/2012 | Mohl et al. | |
| 8,281,786 B2 | 10/2012 | Belson | |
| 8,292,839 B2 | 10/2012 | O'Neill | |
| 8,292,871 B2 | 10/2012 | Shapland et al. | |
| 8,317,715 B2 | 11/2012 | Belleville et al. | |
| 8,353,942 B2 | 1/2013 | Merrill | |
| 8,366,659 B2 | 2/2013 | Ehrenreich et al. | |
| 8,398,589 B2 | 3/2013 | Teeslink et al. | |
| 8,402,968 B2 | 3/2013 | Belson | |
| 8,409,846 B2 | 4/2013 | Hassanein et al. | |
| 8,425,549 B2 | 4/2013 | Lenker et al. | |
| 8,430,861 B2 | 4/2013 | Schwartz et al. | |
| 8,449,449 B2 | 5/2013 | Haarstad et al. | |
| 8,454,634 B2 | 6/2013 | Jahns et al. | |
| 8,480,650 B2 | 7/2013 | Ehrenreich et al. | |
| 8,540,669 B2 | 9/2013 | Ehrenreich et al. | |
| 8,567,407 B1 | 10/2013 | Kimani Mwangi et al. | |
| 8,568,464 B2 | 10/2013 | Dae et al. | |
| 8,578,939 B1 | 11/2013 | Kimani Mwangi et al. | |
| 8,585,678 B2 | 11/2013 | Elkins et al. | |
| 8,604,072 B2 | 12/2013 | Anderson et al. | |
| 8,685,460 B2 | 4/2014 | Anderson et al. | |
| 8,702,649 B2 | 4/2014 | Schwartz et al. | |
| 8,708,996 B2 | 4/2014 | Consigny et al. | |
| 8,715,200 B2 | 5/2014 | Pijls | |
| 8,728,747 B2 | 5/2014 | Shirwan | |
| 8,734,320 B2 | 5/2014 | Haarstad et al. | |
| 8,759,402 B2 | 6/2014 | Gottlieb et al. | |
| 8,771,310 B2 | 7/2014 | Forman et al. | |
| 8,821,438 B2 | 9/2014 | Ehrenreich et al. | |
| 8,822,535 B2 | 9/2014 | Roth et al. | |
| 8,876,850 B1 | 11/2014 | Vollmers et al. | |
| 8,880,185 B2 | 11/2014 | Hastings et al. | |
| 8,888,733 B2 | 11/2014 | Kassab | |
| 8,888,737 B2 | 11/2014 | Vaisnys et al. | |
| 8,945,039 B2 | 2/2015 | Kassab | |
| 8,974,542 B2 | 3/2015 | Fujimoto et al. | |
| 8,993,527 B2 | 3/2015 | Mangano | |
| 9,004,066 B2 | 4/2015 | Belson | |
| 9,012,404 B2 | 4/2015 | Spirio et al. | |
| 9,023,010 B2 | 5/2015 | Chiu et al. | |
| 9,023,831 B2 | 5/2015 | Bansal | |
| 9,040,035 B2 | 5/2015 | Herzberg et al. | |
| 9,060,507 B2 | 6/2015 | Alford et al. | |
| 9,078,682 B2 | 7/2015 | Lenker et al. | |
| 9,078,982 B2 | 7/2015 | Lane et al. | |
| 9,155,869 B2 | 10/2015 | Ehrenreich et al. | |
| 9,168,361 B2 | 10/2015 | Ehrenreich et al. | |
| 9,173,918 B2 | 11/2015 | Zhang et al. | |
| 9,174,020 B2 | 11/2015 | Allen et al. | |
| 9,205,177 B2 | 12/2015 | Schorgl et al. | |
| 9,205,226 B2 | 12/2015 | Allen | |
| 9,216,198 B2 | 12/2015 | Balkus, Jr. et al. | |
| 9,255,133 B2 | 2/2016 | Shirwan | |
| 9,271,964 B2 | 3/2016 | Anderson et al. | |
| 9,289,193 B2 | 3/2016 | Argenta et al. | |
| 9,314,366 B2 | 4/2016 | Platt et al. | |
| 9,320,846 B2 | 4/2016 | Burns et al. | |
| 9,326,972 B2 | 5/2016 | Kohn et al. | |
| 9,402,952 B2 | 8/2016 | Beyersdorf | |
| 9,433,381 B2 | 9/2016 | Mohl et al. | |
| 9,433,761 B2 | 9/2016 | Schwartz et al. | |
| 9,457,179 B2 | 10/2016 | Hassanein et al. | |
| 9,485,983 B2 | 11/2016 | Leybaert | |
| 9,492,468 B2 | 11/2016 | Stover | |
| 9,504,781 B2 | 11/2016 | Kassab et al. | |
| 9,533,124 B2 | 1/2017 | Mack et al. | |
| 9,533,127 B2 | 1/2017 | Michal et al. | |
| 9,550,046 B1 | 1/2017 | Allen et al. | |
| 9,681,875 B2 | 6/2017 | Mohl et al. | |
| 9,844,383 B2 | 12/2017 | Allen | |
| 9,855,049 B2 | 1/2018 | Schiemanck et al. | |
| 9,884,171 B2 | 2/2018 | Ehrenreich et al. | |
| 9,999,718 B2 | 6/2018 | Brady et al. | |
| 10,010,251 B2 | 7/2018 | Manstrom et al. | |
| 10,105,064 B2 | 10/2018 | Manstrom et al. | |
| 10,118,016 B2 | 11/2018 | Schwartz et al. | |
| 10,238,394 B2 | 3/2019 | Mohl et al. | |
| 10,244,951 B2 | 4/2019 | Hiltner | |
| 10,279,104 B2 | 5/2019 | Burns et al. | |
| 10,313,016 B2 | 6/2019 | Fang et al. | |
| 10,315,016 B2 * | 6/2019 | Schwartz | A61M 25/1011 |
| 10,335,539 B2 | 7/2019 | Burns et al. | |
| 10,561,425 B2 | 2/2020 | Schiemanck et al. | |
| 10,716,482 B2 | 7/2020 | Anderson et al. | |
| 10,835,670 B2 | 11/2020 | Burns et al. | |
| 10,842,933 B2 | 11/2020 | Burmaster et al. | |
| 10,952,883 B2 | 3/2021 | Hoem et al. | |
| 11,135,408 B2 | 10/2021 | Schwartz et al. | |
| 11,412,936 B2 | 8/2022 | Hoem et al. | |
| 11,433,183 B2 | 9/2022 | Schwartz et al. | |
| 11,471,596 B2 | 10/2022 | Pile-Spellman et al. | |
| 11,517,318 B2 | 12/2022 | Mohl et al. | |
| 11,602,618 B2 | 3/2023 | De Bruyne et al. | |
| 11,724,030 B2 | 8/2023 | Schwartz et al. | |
| 11,786,140 B2 | 10/2023 | Schwartz | |
| 11,957,854 B2 | 4/2024 | Schwartz et al. | |
| 12,100,516 B2 | 9/2024 | Bernard et al. | |
| 2001/0041862 A1 | 11/2001 | Glickman | |
| 2002/0045893 A1 | 4/2002 | Lane et al. | |
| 2002/0095147 A1 | 7/2002 | Shadduck | |
| 2002/0115982 A1 | 8/2002 | Barbut et al. | |
| 2003/0018273 A1 | 1/2003 | Corl et al. | |
| 2003/0047777 A1 | 3/2003 | In't Zandt et al. | |
| 2004/0181206 A1 | 9/2004 | Chiu et al. | |
| 2004/0230131 A1 | 11/2004 | Kassab et al. | |

(56) References Cited

U.S. PATENT DOCUMENTS

| | | |
|---|---|---|
| 2004/0260333 A1 | 12/2004 | Dubrul et al. |
| 2005/0049451 A1 | 3/2005 | Schock et al. |
| 2005/0059931 A1 | 3/2005 | Garrison et al. |
| 2005/0245894 A1 | 11/2005 | Zadno-Azizi |
| 2005/0245897 A1 | 11/2005 | Bolduc et al. |
| 2005/0267561 A1 | 12/2005 | Jones et al. |
| 2006/0184089 A1 | 8/2006 | Makower et al. |
| 2008/0300573 A1 | 12/2008 | Consigny et al. |
| 2009/0177183 A1 | 7/2009 | Pinkernell et al. |
| 2010/0121204 A1 | 5/2010 | Utsuno et al. |
| 2010/0143317 A1 | 6/2010 | Pecora et al. |
| 2010/0168649 A1 | 7/2010 | Schwartz et al. |
| 2010/0249704 A1 | 9/2010 | Wagner |
| 2010/0280451 A1 | 11/2010 | Teeslink et al. |
| 2011/0040319 A1 | 2/2011 | Fulton, III |
| 2011/0196255 A1 | 8/2011 | Kassab |
| 2012/0072190 A1 | 3/2012 | Sharma et al. |
| 2012/0157913 A1 | 6/2012 | Aziz et al. |
| 2012/0265079 A1 | 10/2012 | Hilmersson |
| 2012/0265283 A1 | 10/2012 | Mack et al. |
| 2012/0276152 A1 | 11/2012 | Hossainy et al. |
| 2013/0035560 A1 | 2/2013 | Anand et al. |
| 2013/0131523 A1 | 5/2013 | Suchecki et al. |
| 2013/0132054 A1 | 5/2013 | Sharma et al. |
| 2013/0150737 A1 | 6/2013 | Schwartz et al. |
| 2013/0165858 A1 | 6/2013 | Cox et al. |
| 2013/0282097 A1 | 10/2013 | Burton |
| 2014/0155684 A1 | 6/2014 | Ehrenreich |
| 2014/0323887 A1 | 10/2014 | Anderson et al. |
| 2015/0018928 A1 | 1/2015 | Sachar et al. |
| 2015/0133799 A1 | 5/2015 | O'Connell et al. |
| 2015/0141853 A1 | 5/2015 | Miller, III et al. |
| 2016/0082178 A1 | 3/2016 | Agah et al. |
| 2016/0199003 A1 | 7/2016 | McCaffrey et al. |
| 2016/0213834 A1 | 7/2016 | Brady et al. |
| 2016/0270731 A1 | 9/2016 | Burkett |
| 2016/0361068 A1 | 12/2016 | Mohl et al. |
| 2016/0367785 A1 | 12/2016 | Schwartz et al. |
| 2017/0119260 A1 | 5/2017 | Gilbert |
| 2017/0189654 A1 | 7/2017 | Schwartz et al. |
| 2017/0290598 A1 | 10/2017 | Culbert et al. |
| 2018/0085519 A1 | 3/2018 | McCaffrey et al. |
| 2018/0146864 A1* | 5/2018 | Jansen ................. A61B 5/0215 |
| 2018/0185576 A1 | 7/2018 | Burns et al. |
| 2018/0280172 A1 | 10/2018 | Hoem et al. |
| 2018/0353681 A1 | 12/2018 | Burmaster et al. |
| 2019/0046760 A1 | 2/2019 | Schwartz et al. |
| 2019/0078914 A1 | 3/2019 | Doering et al. |
| 2019/0082976 A1 | 3/2019 | Hoem et al. |
| 2019/0275248 A1 | 9/2019 | Schwartz et al. |
| 2019/0290889 A1 | 9/2019 | De Bruyne et al. |
| 2019/0358437 A1 | 11/2019 | Schwartz et al. |
| 2020/0093991 A1 | 3/2020 | Schwartz et al. |
| 2020/0282189 A1 | 9/2020 | Gaynor |
| 2020/0284632 A1 | 9/2020 | Abed et al. |
| 2020/0284668 A1 | 9/2020 | Razavidinani et al. |
| 2020/0284675 A1 | 9/2020 | Jamali |
| 2020/0284677 A1 | 9/2020 | Wagner |
| 2020/0316348 A1 | 10/2020 | Ascher et al. |
| 2020/0383688 A1 | 12/2020 | Olson et al. |
| 2021/0085932 A1 | 3/2021 | Oezer |
| 2021/0228387 A1 | 7/2021 | Hoem et al. |
| 2021/0361170 A1 | 11/2021 | Schwartz et al. |
| 2021/0366620 A1 | 11/2021 | Bernard et al. |
| 2022/0016399 A1 | 1/2022 | Schwartz et al. |
| 2022/0062214 A1 | 3/2022 | Pantos et al. |
| 2022/0218210 A1 | 7/2022 | Schwartz et al. |
| 2022/0378301 A1 | 12/2022 | Schwartz et al. |
| 2023/0381415 A1 | 11/2023 | Schwartz et al. |
| 2024/0269440 A1 | 8/2024 | Schwartz et al. |

FOREIGN PATENT DOCUMENTS

| | | | |
|---|---|---|---|
| CN | 1182374 A | 5/1998 | |
| CN | 201058169 Y | 5/2008 | |
| CN | 101356286 A | 1/2009 | |
| CN | 102125721 A | 7/2011 | |
| CN | 102596010 A | 7/2012 | |
| CN | 102740902 A | 10/2012 | |
| CN | 102811758 A | 12/2012 | |
| CN | 103153212 A | 6/2013 | |
| CN | 103228317 A | 7/2013 | |
| CN | 103298441 A | 9/2013 | |
| CN | 103826690 A | 5/2014 | |
| CN | 105636512 A | 6/2016 | |
| CN | 105848573 A | 8/2016 | |
| CN | 105879008 A | 8/2016 | |
| CN | 106132309 A | 11/2016 | |
| CN | 106310495 A | 1/2017 | |
| CN | 108778149 A | 11/2018 | |
| EP | 0363203 A2 | 4/1990 | |
| EP | 0405831 A2 | 1/1991 | |
| EP | 2497520 A1 | 9/2012 | |
| EP | 2793992 B1 | 9/2015 | |
| EP | 2073884 B1 | 10/2018 | |
| EP | 3399923 A1 | 11/2018 | |
| EP | 3399923 A4 | 8/2019 | |
| EP | 3705034 A1 | 9/2020 | |
| GB | 2541368 A | 2/2017 | |
| GB | 2577472 A | 4/2020 | |
| JP | H10500587 A | 1/1998 | |
| JP | H11178929 A | 7/1999 | |
| JP | 2006187620 A | 7/2006 | |
| JP | 2008173137 A | 7/2008 | |
| JP | 2008264134 A | 11/2008 | |
| JP | 2009514596 A | 4/2009 | |
| JP | 2009233175 A | 10/2009 | |
| JP | 2012200573 A | 10/2012 | |
| JP | 2013146505 A | 8/2013 | |
| JP | 2013534845 A | 9/2013 | |
| JP | 2014069034 A | 4/2014 | |
| JP | 2015522347 A | 8/2015 | |
| JP | 2016507272 A | 3/2016 | |
| JP | 2016168151 A | 9/2016 | |
| JP | 2016215836 A | 12/2016 | |
| WO | WO-9600596 A1 | 1/1996 | |
| WO | WO-1999044666 A2 | 9/1999 | |
| WO | WO-0128419 A2 | 4/2001 | |
| WO | WO-0170325 A2 | 9/2001 | |
| WO | WO-02085443 A1 | 10/2002 | |
| WO | WO-2004062526 A2 | 7/2004 | |
| WO | WO-2004080508 A2 | 9/2004 | |
| WO | WO-2006059317 A1 | 6/2006 | |
| WO | WO-2008088579 A2 | 7/2008 | |
| WO | WO-2010105356 A1 | 9/2010 | |
| WO | WO-2011161212 A1 * | 12/2011 | ......... A61B 5/02152 |
| WO | WO-2013055896 A1 | 4/2013 | |
| WO | WO-2014022935 A1 | 2/2014 | |
| WO | WO-2014106158 A1 | 7/2014 | |
| WO | WO-2015108928 A1 | 7/2015 | |
| WO | WO-2015150913 A2 | 10/2015 | |
| WO | WO-2017004432 A1 | 1/2017 | |
| WO | WO-2017078693 A1 | 5/2017 | |
| WO | WO-2017078694 A1 | 5/2017 | |
| WO | WO-2017120229 A1 | 7/2017 | |
| WO | WO-2017160270 A1 | 9/2017 | |
| WO | WO-2017210584 A1 | 12/2017 | |
| WO | WO-2018175485 A1 | 9/2018 | |
| WO | WO-2019060421 A1 | 3/2019 | |
| WO | WO-2019173758 A1 | 9/2019 | |
| WO | WO-2019232452 A1 | 12/2019 | |
| WO | WO-2020061507 A1 | 3/2020 | |
| WO | WO-2021035190 A1 | 2/2021 | |
| WO | WO-2021234670 A1 | 11/2021 | |
| WO | WO-2022147318 A1 | 7/2022 | |
| WO | WO-2022149106 A1 | 7/2022 | |

OTHER PUBLICATIONS

Extended European Search Report dated Jul. 19, 2019 in EP Patent Appl. Serial No. 17736254.8 (0130).

(56)          References Cited

OTHER PUBLICATIONS

International Search Report and Written Opinion dated Jan. 3, 2019 in Int'l PCT Patent Application Serial No. PCT/US2018/051760 (0310).

International Search Report and Written Opinion dated Mar. 17, 2017 in Int'l PCT Patent Application Serial No. PCT/US2017/012181 (0110).

International Search Report and Written Opinion dated May 25, 2018 in Int'l PCT Patent Application Serial No. PCT/US2018/023422 (0210).

International Search Report and Written Opinion dated Jul. 3, 2019 in Int'l PCT Patent Application Serial No. PCT/US2019/021426 (0410).

International Search Report and Written Opinion dated Oct. 1, 2019 in Int'l PCT Patent Application Serial No. PCT/US2019/035020 (0510).

International Search Report and Written Opinion dated Nov. 27, 2019 in Int'l PCT Patent Application Serial No. PCT/US2019/052245 (0610).

Lindsey, et al., "Guidelines for Experimental Models of Myocardial Ischemia and Infarction," American Journal of Physiology-Heart and Circulatory Physiology, 314(4):H812-H838 (Apr. 2018).

Liu, JingHua, Coronary Heart Disease: Anatomy, Function and Imaging, Peking Union Medical College Press, Apr. 30, 2013, p. 56.

Qiu, et al., "Microvasculature-on-a-Chip for the Long-term Study of Endothelial Barrier Dysfunction and Microvascular Obstruction in Disease," Nature Biomedical Engineering, 2(6):453-463 (Apr. 2018).

Supplementary European Search Report dated Apr. 24, 2020 in EP Patent Appl. Serial No. 18771178.3 (0230).

Tsai, et al., "In Vitro modeling of the microvascular occlusion and thrombosis that occur in hematologic diseases using microfluidic technology," Journal of Clinical Investigation, 122(1):408-418 (Jan. 2012).

International Search Report & Written Opinion dated Apr. 7, 2022 in Int'l PCT Patent Appl. Serial No. PCT/IB2022/050152 (0810).

International Search Report & Written Opinion dated Aug. 9, 2021 in Int'l PCT Patent Appl. Serial No. PCT/IB2021/054453 (0710).

AU Application No. 2021274173, Office Action mailed Dec. 5, 2025; Applicant Colfrow Therapeutics AG, 4 pages.

Chung et al. "Microfluidic fabrication of microengineered hydrogels and their application in tissue engineering." Lab on a Chip. 2012;12(1):45-59.

JP Application No. 2022-571210, Office Action for dated Jan. 20, 2025; Applicant Colfrow Therapeutics AG; with English translation 27 pages.

JP Application No. 2022-571210, Office Action mailed Jul. 30, 2025; Applicant Colfrow Therapeutics AG., with English Translation; 7 pages.

Kim et al. "Vasculature-on-a-chip for in vitro disease models." Bioengineering. Jan. 24, 2017;4(1):8; 18 pages.

Malinowski et al. "Large animal model of acute right ventricular failure with functional tricuspid regurgitation." International Journal of Cardiology. Aug. 1, 2018;264:124-129.

Meier et al. "Coronary wedge pressure in relation to spontaneously visible and recruitable collaterals." Circulation. May 1987;75(5):906-913.

PCT Application No. PCT/IB2021/054453, International Preliminary Report on Patentability mailed Nov. 17, 2022, Applicant Colfrow Therapeutics AG; 8 pages.

Urban et al. "Coronary wedge pressure: a predictor of restenosis after coronary balloon angioplasty." Journal of the American College of Cardiology. Sep. 1987;10(3):504-509.

Wahab A. "Interpolation and Extrapolation." Proc. Topics Syst. Eng. Jan. 2017; 17:1-6.

\* cited by examiner

100

102

103

101

104

105

From 7A

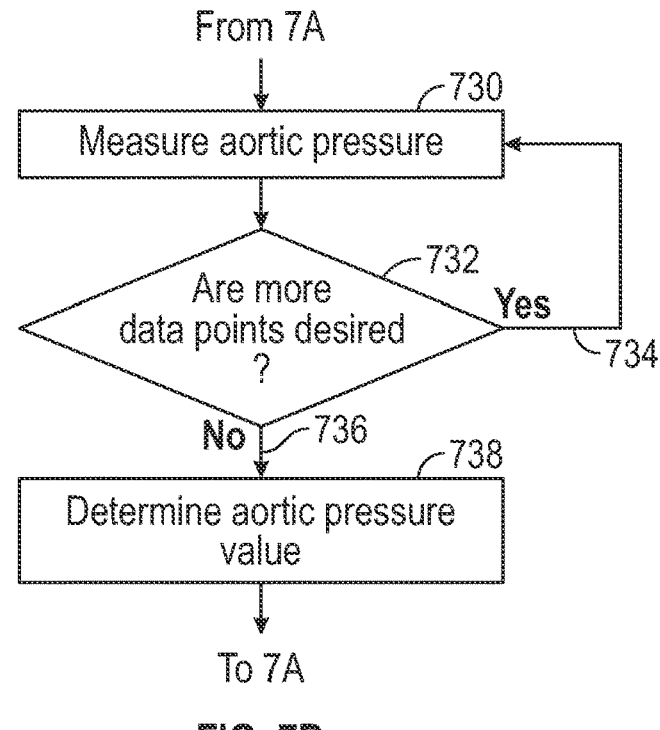

730 Measure aortic pressure

732 Are more data points desired ?

Yes 734

No 736

738 Determine aortic pressure value

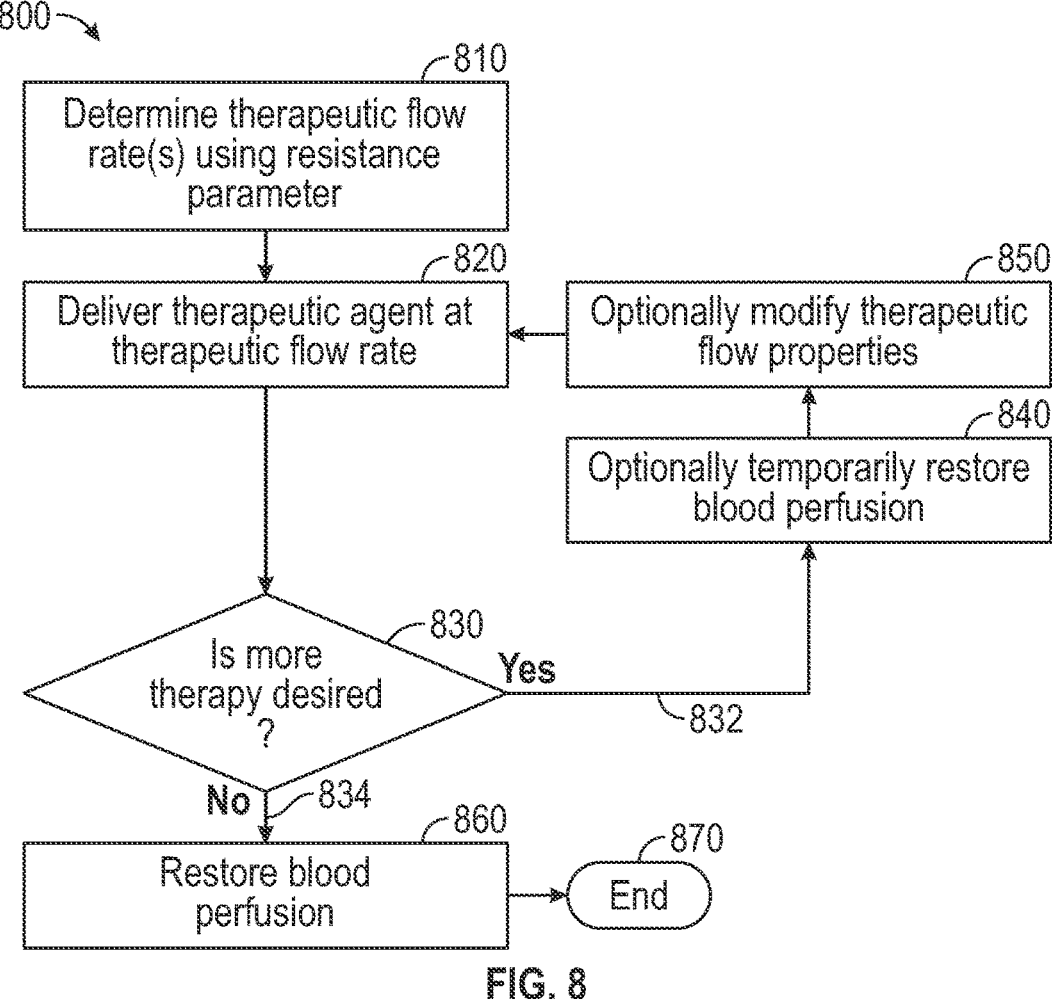

810 Determine therapeutic flow rate(s) using resistance parameter

820 Deliver therapeutic agent at therapeutic flow rate

850 Optionally modify therapeutic flow properties

840 Optionally temporarily restore blood perfusion

830 Is more therapy desired ?

Yes 832

No 834

860 Restore blood perfusion

870 End

FIG. 8

| Pump Flow $Q_{pump}$ | 0 ml / min | 5 ml / min | 10 ml / min | 20 ml / min | 30 ml / min |
|---|---|---|---|---|---|
| Mean Distal Pressure $P_d$ | 21.097 mmHg | 26.771 mmHg | 28.482 mmHg | 33.287 mmHg | 34.720 mmHg |
| Regression Parameters | Slope = 0.311907 mmHg·min/ml, Y-axis Intercept = 25.92522 mmHg, $R^2$ = 0.911183 | | | | |

CONTROLLED FLOW INFUSION MICROVASCULAR DYSFUNCTION DIAGNOSTIC AND THERAPY

CLAIM OF PRIORITY AND RELATED APPLICATIONS

This application claims the benefit of and priority to U.S. Provisional Patent Application Ser. No. 63/029,152, filed on May 22, 2020, titled Controlled Flow Infusion Microvascular Dysfunction Diagnostic and Therapy, which is hereby incorporated by reference in its entirety. This application also incorporates by reference the entirety of the following: U.S. Pat. No. 10,315,016 to Schwartz et al., issued Jun. 11, 2019, and titled System and methods for treating MVO; U.S. Pat. No. 10,952,883 to Hoem et al., issued Mar. 23, 2021, and titled Combined stent reperfusion system; U.S. Patent Application Pub. No. 2019/0082976 to Hoem et al., filed Mar. 21, 2019, and titled Intracoronary Characterization of Microvascular Obstruction (MVO) and Myocardial Infarction; U.S. Patent Application Pub. No. 2019/0275248 to Schwartz et al., filed Sep. 12, 2019, and titled System for Diagnosing and Treating Microvascular Obstructions; International Patent Application No. PCT/US2019/035020 to Bernard et al., published on Dec. 5, 2019 as International Publication No. WO 2019/232,452, and titled Microfluidic Coronary Circulatory Model; and U.S. Patent Pub. No. 2020/0093991 to Schwartz et al., filed Mar. 26, 2020, and titled Method and Apparatus for Diagnosis and Treatment of Microvascular Dysfunction; U.S. Provisional Patent Application Ser. No. 63/136,174, filed on Jan. 11, 2021, and titled Apparatus and Method for Determining and/or Treating Microvascular Obstruction.

TECHNICAL FIELD

Methods and devices are provided for the diagnosis and/or treatment of microvascular function and dysfunction (MVD), including microvascular obstructions (MVO), and other diseases of the microvasculature of organs, including the heart.

BACKGROUND

Heart attack or acute ECG ST segment elevation myocardial infarction ("STEMI") is caused by sudden occlusion of an epicardial coronary artery, typically by a fibrin and platelet rich clot, with associated embolic plaque and debris. Electrocardiographic signs of acute transmural myocardial infarction (heart attack) are ST segment elevation manifesting across multiple anatomic ECG leads. ST segment elevation is a hallmark of severe coronary artery occlusion or narrowing, which causes ischemic myocardial injury and cell death. Large vessel occlusion often is associated with small vessel severe stenosis or occlusion (referred to as microvascular occlusion or MVO), hemodynamic collapse, clot with embolic debris, and other effects that reduce blood supply. MVO is an independent predictor of late adverse events, including death and heart failure, with no successful MVO therapy identified to date.

Interventional Cardiology is proficient at opening severely narrowed or occluded epicardial coronary arteries using catheters, guide wires, balloons, and stents in a cardiac catheterization laboratory. However, microvascular obstruction cannot be diagnosed nor treated in the catheter laboratory. Moreover, effective treatment options for MVO typically are extremely limited even when it is accurately diagnosed.

Heart muscle salvage (i.e., saving muscle from necrosis caused by ischemia) is of critical concern to ensure good long-term outcomes in patients suffering STEMI. A key component of achieving positive long-term outcome requires minimizing the interval between onset of coronary artery occlusion (at home or outside the hospital) and re-opening the occluded artery in a catheter laboratory. Interventional Cardiologists can reduce the duration of artery occlusion time by implementing streamlined and efficient emergency medical systems. The goal of such procedures is to bring STEMI patients to the catheterization laboratory as soon as possible, thereby avoiding long-term STEMI complications. Complications resulting from STEMI and MVO include systolic and diastolic heart failure, arrhythmias, aneurysms, ventricular rupture and multiple other serious complications. These complications can markedly shorten life and/or impose severe limitations on quality of life.

Modern interventional therapy for acute myocardial infarction has matured over time with impressive clinical results. In recent years, heart attack/STEMI death rates at 30 days post event have dropped from more than 30% to less than 5%. This improvement has been achieved by reperfusing the heart with blood as soon as possible after coronary arterial occlusion, which in turn has resulted by streamlining clinical care systems to open coronary arteries in the catheterization lab as rapidly as possible after heart attack onset. Emergency procedures, including stenting and balloon angioplasty, indisputably have improved early and late clinical results of acute heart attack therapy.

However, substantial challenges remain for treating STEMI patients and reducing long-term complications. These problems include heart failure (poor cardiac function and cardiac enlargement), cardiac/ventricular rupture, persistent ischemic chest pain/angina, left ventricular aneurysm and clot, and malignant arrhythmias.

Late heart failure complicates 25-50% of STEMI cases, and consists of poor left ventricular function and damaged myocardium. Heart failure typically worsens as the heart remodels in shape and size, with associated functional loss. Nearly half of all new heart failure in patients under 75 years is linked to STEMI.

Many years investigating STEMI therapy show that opening the epicardial/large coronary artery is insufficient to salvage heart muscle and improve long-term patient outcomes. A very common reason for poor late results after heart attack is microvascular obstruction (MVO). MVO is occlusion or severe flow limitation in the small, internal cardiac microvessels. These microvessels are too small and unreachable to stent or be treated with conventional drug/thrombolytic therapy due to microvessels' size and number. Thus, despite widely patent epicardial coronary arteries, residual MVO obstructs blood flow to the myocardium, resulting in ischemia and tissue necrosis and severe long-term heart muscle damage.

MVO thus remains a critical frontier in cardiology. Cardiac microvessels comprise small arteries, arterioles, capillaries and venules that are frequently collapsed and filled with cells, clot and debris (platelets, fibrin, and embolic plaque material) during STEMI. Too often, obstructed microvessels (MVO) do not resolve even after stent placement and present serious long-term negative prognostic implications.

MVO is very common in STEMI patients, even though stenting and balloon angioplasty are successful at opening epicardial coronary arteries. MVO occurs in more than half of all STEMI patients, even with good blood flow through open the epicardial arteries and newly placed stents.

MVO extent is key to the severity of myocardial damage and patient outcome. MVO may be accurately detected and measured only via cardiac MRI imaging, which identifies MVO location, extent and severity. MRI, however, cannot be performed emergently or during cardiac catheterization procedures, as it requires patients to be located in a separate imaging area, may require up to 1 hour to complete, and is a separate, expensive procedure.

Important features of MVO may be summarized by the following:

1. MVO and microvascular dysfunction in STEMI are principal causes of early and late major complications after heart attack.

2. Angiographic "no-reflow" or "low-reflow" is caused by MVO, i.e., obstructed microvessels within the heart muscle. MVO in severe cases is characterized fluoroscopically by very slow radiographic contrast filling and flow in the epicardial coronary arteries, as visualized during coronary treatment in the catheterization laboratory. Radiographic contrast filling, however, is only able to diagnose severe no-reflow cases and thus is not able to detect MVO in the majority of the patients.

3. MVO causes myocardial cell injury and death from prolonged ischemia, which deprives the tissue of oxygen, blood flow, and replenishment of key metabolic nutrients, such as glucose. MVO microscopic analysis shows collapsed microvessels with red cells, platelet and fibrin clot, dead myocardial cells, inflammatory cells, myocyte cell death, and endothelial cell death along the obstructed intramyocardial capillaries.

4. Acute MVO manifests as cardiac arterioles and capillaries completely occluded by platelet and fibrin-rich thrombus, platelet-neutrophil aggregates, dying blood cells and embolic debris, and small vessel collapse due to very low intraluminal pressure caused by the occlusion.

5. When MVO complicates acute STEMI/myocardial infarction, far greater heart/myocardial damage occurs, and poor ventricular function occurs early.

6. MVO is very common. It occurs in (a.) roughly 53% of all STEMI and non-ST segment elevation myocardial infarction (NSTEMI) regardless of epicardial flow, (b.) 90% of Large Transmural STEMI, (c.) 40% of MI with TIMI III (normal) X-ray visualized flow, and (d.) MVO is the single most potent prognostic marker of events after controlling for infarct size.

7. Patients with microvascular obstruction have more late major adverse cardiovascular events (MACE) than those without MVO (45% versus 9%).

8. MVO is the best predictor of acute and chronic cardiovascular adverse outcomes.

9. MVO acutely becomes late fibrous scar and causes poor cardiac function.

MVO cannot be effectively diagnosed and measured in a conventional catheterization laboratory. Moreover, no effective conventional therapies currently are commercially available. Previously proposed therapies have proved essentially ineffective, and in some cases, dangerous.

A major complication from myocardial infarction is cell death or ischemia. Myocardial infarction may cause short, but profound ischemia, which is reversible ("stunning"), chronic ischemia that occurs when myocardial cells are alive but without sufficient oxygen or nutrients to contract normally ("hibernation"); or necrosis and infarction via prolonged ischemia. Infarction typically spreads as a wave, beginning in the endocardium and spreading across the myocardial wall. Each of these events can be characterized by noninvasive imaging and testing, such as nuclear, echo, and PET methods. An exceptionally good test is provided by cardiac MRI, in which gadolinium contrast may be used to visualize the microvascular obstruction.

Myocardial infarction (MI) resulting in microvascular obstruction has profound clinical impact. While epicardial coronary arterial occlusion is well known, it has been hypothesized that microscopic/microvascular plugging by thrombus-platelets and fibrin of the microvasculature also occurs. Histopathologic studies show endothelial cell edema, with fibrin and platelet aggregation in both human cases and in animal models. Microvascular plugging also occurs due to red blood cells, white cells and fibrin-platelet aggregates, not visible to light microscopy, may occur, but can be seen via immunostains and EM/SEM/TEM. To date, heterotopic platelet aggregation is possible but unproven.

MVO is only one disorder of several disorders under a larger classification of microvascular dysfunction. Microvascular dysfunction also occurs in patients without epicardial artery occlusion, and encompasses a much larger patient population than the acute coronary occlusion (STEMI) patient group. The effects of occlusion of vessels less than 200 microns in diameter in patients without epicardial artery (vessels larger than 2 mm) occlusion are poorly understood despite years of study and many failed therapeutic strategies.

There is therefore a need in the art for apparatus and methods that can more accurately assess microvascular function and dysfunction in the larger MVD patient population. Such apparatus and methods may benefit patients by providing a more accurate diagnosis and treatment. There is also a need in the art for apparatus and methods that can more accurately diagnose, quantify, and treat microvascular dysfunction, including microvascular obstruction. Still further, there is a need for apparatus and methods to diagnose and, if necessary, treat MVO that may be present in the microvasculature downstream of where a stent has been deployed.

SUMMARY

Methods and apparatus are provided for more accurate assessment, diagnosis and/or treatment of microvascular dysfunction. In various embodiments, the microvascular dysfunction may include clinical syndromes such as STEMI/NSTEMI, microvascular obstruction, no-reflow, cardiogenic shock, and other dysfunctional diseases of the microvasculature. The principles of the present invention are applicable to diagnosis and/or treatment of many organs, including the heart. More particularly, non-limiting embodiments include devices and methods to successfully diagnose, restore patency, re-open and preserve flow, and/or limit reperfusion injury in vessels and organs with microvascular dysfunction. Applications include, but are not limited to, therapy for organ systems including the heart (acute myocardial infarction—primary percutaneous coronary intervention (PPCI)), brain (stroke (CVA)), bowel ischemia/infarction, pulmonary emboli/infarction, critical limb ischemia/infarction, kidney/renal ischemia/infarction, liver, peripheral vascular, neurovascular and others.

In accordance with one aspect of the present invention, a system is provided that includes a specialized infusion and sensing catheter for delivering diagnostic and/or therapeutic agents, and a control console. The control console is programmed with specialized algorithms that can be used to diagnose and/or treat microvascular dysfunction by determining parameters that may be used to indicate physiologic events, such as microvascular obstruction, myocardial infarction, and myocardial ischemia. Methods of operating the inventive system to diagnose and/or treat microvascular dysfunction, such as MVO, also are provided.

Systems and apparatus are included that are configured to perform microvascular function assessment. The inventive systems and apparatus also may be used to diagnose and treat microvascular dysfunction, such as microvascular obstruction (MVO). In accordance with one aspect of the invention, the system and apparatus are configured to diagnose and, if necessary, treat MVO that may be present in the microvasculature downstream of where a stent has been deployed.

Methods for determining the presence of a microvascular dysfunction, such as MVO, of a patient also are provided. These methods include delivering a fluid into a vessel of the patient at known flow delivery rates, measuring the resulting pressures associated with the known delivery rates, and determining a relationship between the flow delivery rates and corresponding arterial pressures, such as a linear relationship. The methods also include measuring the patient's aortic pressure and compensating for a collateral flow rate. The methods also include using a pressure and flow rate sufficient to negate a collateral flow rate as a resistance parameter that may be used for diagnostic purposes, such as to determine the existence and/or extent of an MVO, as well as for therapeutic purposes to determine a treatment. In some methods, the treatment includes the delivery of a therapeutic agent into the vessel at a plurality of delivery flow rates determined by the resistance parameter.

The inventive system includes systems or apparatus for assessing microvascular dysfunction of a patient and, optionally, providing treatment of the MVD. Some systems or apparatus include a catheter having an occlusion system, pressure sensor located distal and, optionally, proximal to the occlusion system, and a lumen to deliver fluid and, optionally, a therapeutic agent. The systems and apparatus further include a computerized infusion system that is configured to communicate with the sensors and use the sensor readings along with known fluid delivery rates corresponding to the sensor readings to determine a resistance parameter, such as may be used to indicate the presence of an MVO. Systems and apparatus may further deliver one or more therapeutic agents at a delivery rate or rates determined by the resistance parameter. In accordance with one aspect of the invention, the resistance parameter may be used with MRI results to predict MVO.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. It should be noted that the drawings are not necessarily to scale; emphasis instead is placed on illustrating the principles of the inventive concepts. Also, in the drawings, like reference characters may refer to the same parts or similar parts throughout the different views. It is intended that the embodiments and figures disclosed herein are to be considered illustrative rather than limiting.

FIGS. 7A and 7B are flow charts for performing a diagnosis in accordance with the principles of the present invention;

FIG. 8 is a flow chart for providing therapeutic treatment in accordance with the principles of the present invention;

DETAILED DESCRIPTION

The present invention is directed to devices, systems and methods for implementing techniques to determine parameters for predicting physiologic events, and is applicable to diagnosis and/or treatment of many organs, including the heart. More particularly, the inventive systems and methods enable successful prediction of physiologic events, such as microvascular obstruction, myocardial infarction, and myocardial ischemia. Applications of the inventive system and methods include diagnosis and treatment of the heart (acute myocardial infarction—primary percutaneous coronary intervention (PPCI)), brain (stroke (CVA)), bowel ischemia/infarction, pulmonary emboli/infarction, critical limb ischemia/infarction, renal ischemia/infarction, liver, peripheral vascular, neurovascular and others obstruction (MVO) and tissue necrosis/infarction.

Figure 1:
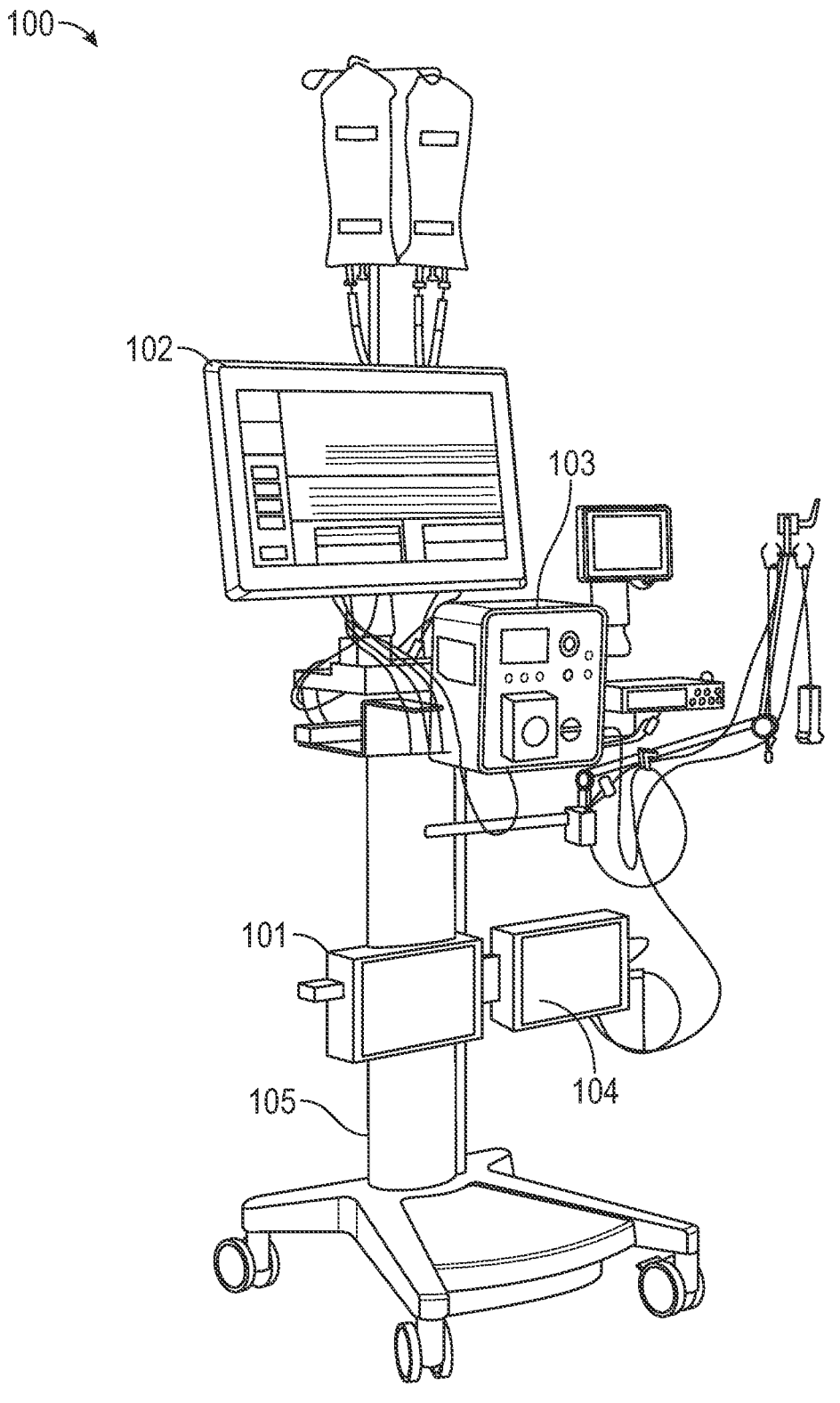
FIG. 1 is a perspective view of an exemplary modular system for assessment of MVD in accordance with principles of the present invention.

Referring to FIG. 1, exemplary modular computerized diagnostic and infusion system 100 for coronary and other human/animal vasculature and organs is described. Infusion system 100 illustratively is packaged as a mobile console and is programmed to enable prediction of physiologic events, including real-time or near real time measurement of coronary artery pressure and flow; pressure/flow time parameters; coronary physiology measures such as micro-vascular resistance determinations. Infusion system 100 includes controller 101, display 102, infusion pump 103, and pressure measurement system 104, all mounted on mobile platform 105.

Figure 2A:
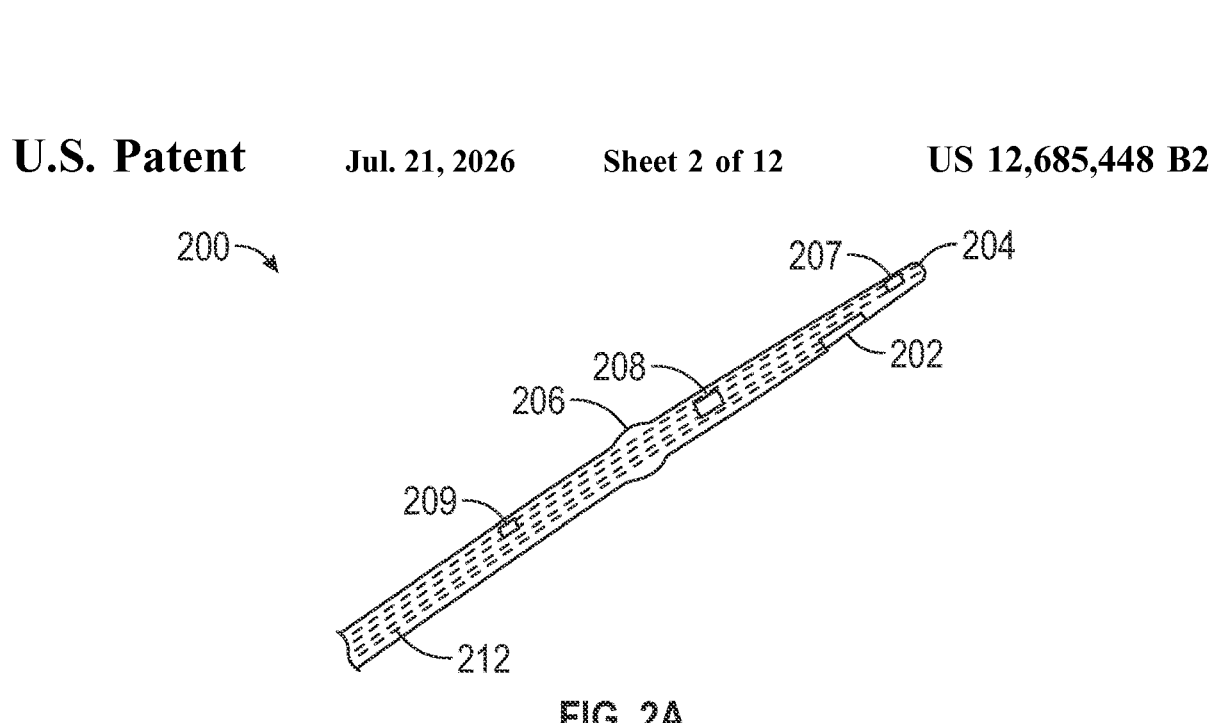
FIGS. 2A-2C are perspective views of distal ends of alternative embodiments of infusion catheters constructed in accordance with the present invention.

Referring now to FIG. 2A, a distal end of exemplary infusion catheter 200 is described. Infusion catheter 200 includes infusion port 202 in fluid communication with infusion lumen 212 that extends from a proximal portion of the catheter and couples to infusion pump 103. Guidewire lumen 204 extends through catheter 200 to permit the infusion catheter to be advanced along a guidewire to a desired position within a patient's vasculature. Catheter 200 may have an enlarged diameter section 206, which serves to increase hydrodynamic resistance for diagnostic purposes. When exposed to fluid flow, section 206 creates a hydro-static pressure gradient within a bodily lumen. Pressure sensor 208, located in the body of catheter 200, may be coupled to pressure measurement system 104 to determine the pressure of a fluid flow within a patient's vasculature. Pressure sensor 207 and pressure sensor 209, also located in the body of catheter 200, may be coupled to pressure measurement system 104 to determine the pressure of a fluid flow. In this embodiment, pressure sensor 207 is located distal to pressure sensor 209.

Figure 2B:
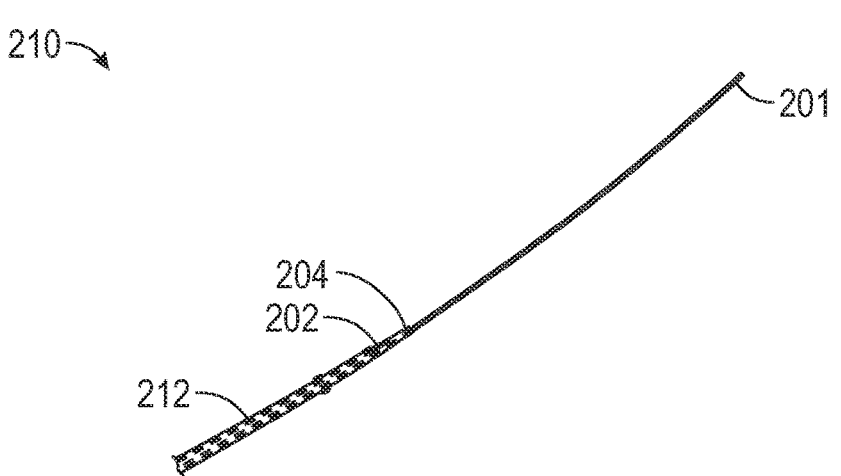

With respect to FIG. 2B, a distal end of an alternative embodiment of an infusion catheter, catheter 210 is described. Guidewire 201, which may be a 0.014" pressure measuring guidewire, may be inserted through catheter 210 in a rapid-exchange (RX) manner so that a distal end of guidewire 201 extends from guidewire lumen exit 204. Infusion port 202 is located on the distal end of catheter 201 adjacent guidewire lumen exit 204 deliver fluids via infusion lumen 212, shown in dotted line.

Figure 2C:
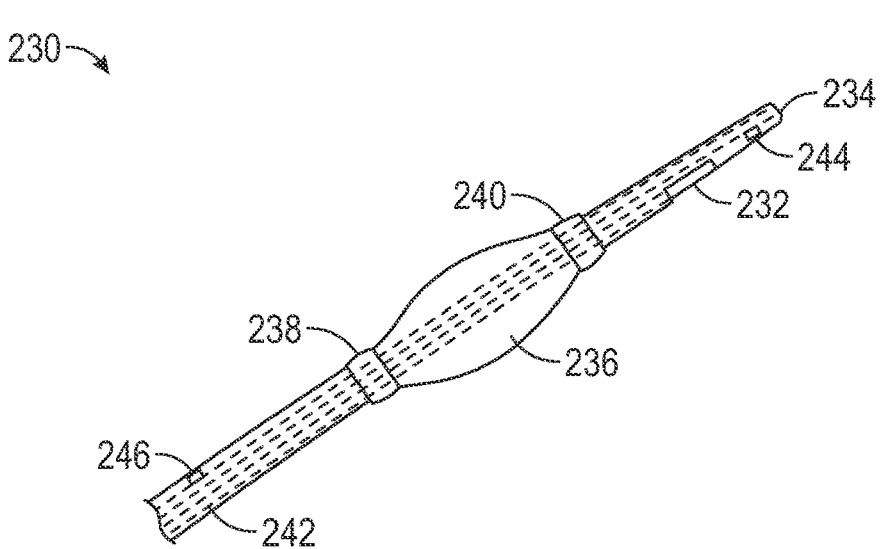

In FIG. 2C, a distal end of another alternative embodiment is described, in which infusion catheter 230 has occlusion balloon 236, radio-opaque markers 238 and 240. Infusion outlet port 232 is disposed in fluid communication with infusion lumen 242, shown in dotted line. Guidewire lumen 234 also is provided and may be arranged for either over-the-wire or rapid exchange use. Pressure sensor 244 and pressure sensor 246, located in the body of catheter 230, may be coupled to pressure measurement system 104 to determine the pressure of a fluid flow. In this embodiment, pressure sensor 244 is located distal to occlusion balloon 236, whereas pressure sensor 246 is located proximal to occlusion balloon 236. Additional embodiments of infusion catheters may be used herein, such as those described in U.S. Pat. No. 10,315,016 to Schwartz or U.S. Patent Application Publication No. 2018/0280172 to Hoem, the entire contents of each of which are incorporated herein by reference.

Figure 3A:
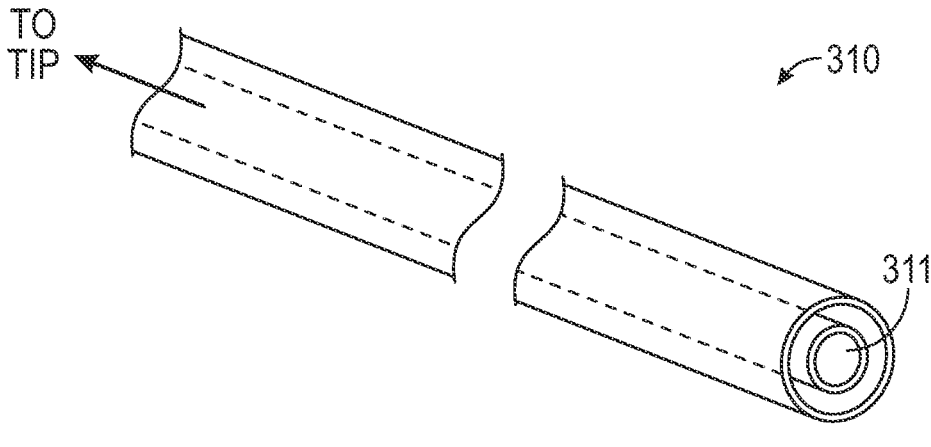
FIG. 3A is perspective view of a central portion of an infusion catheter suitable for use with the distal ends depicted in FIGS. 2A-2D.

Referring now to FIG. 3A, a central portion of an infusion catheter constructed in accordance with principles of the present invention is described. The central portion of catheter 310 includes infusion lumen 312 that encircles guidewire lumen 311, illustratively co-axially. In alternative embodiments, infusion lumen 312 may be arranged side-by-side, or otherwise, with respect to guidewire lumen 311. In preferred embodiments, the diameter of catheter 310 is small, thereby allowing the catheter to be introduced into smaller vessels for diagnosis and therapy. Guidewire lumen 311 preferably has a diameter sufficient to accept a guide wire that provides pressure sensing.

Figure 3B:
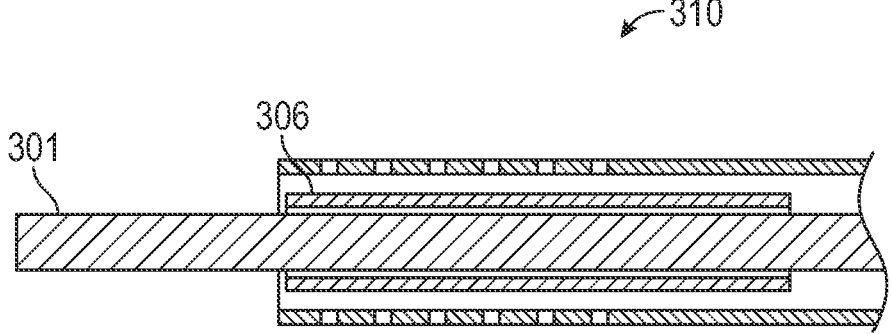
FIGS. 3B and 3C are, respectively, a side sectional view and perspective view of an alternative embodiment of a distal portion of an infusion catheter having a pressure chamber.
Figure 3C:
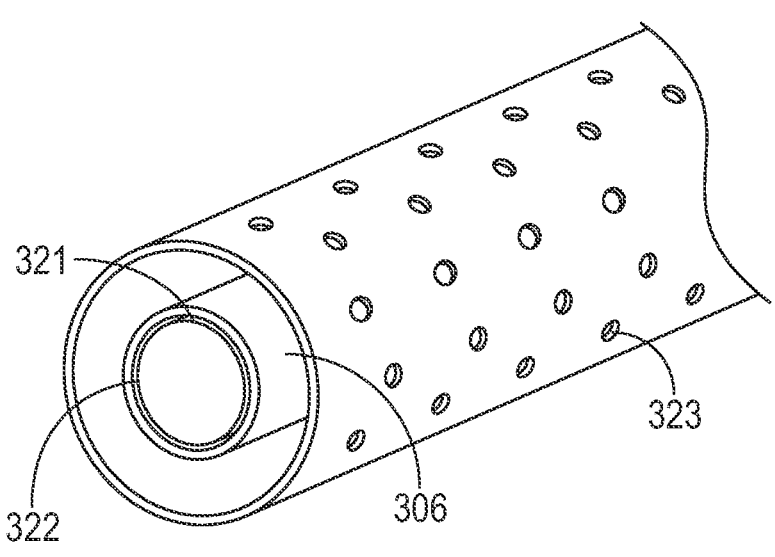

In FIGS. 3B and 3C, a distal portion of an exemplary infusion catheter having pressure chamber 306 disposed on guidewire 301 is described. Pressure chamber 306 is designed to provide a region of stable pressure measurement in a distal arterial segment, and permits pressure measurement at locations different than near or distal to the catheter tip. In some preferred embodiments, multiple pressure chambers may be provided, including a first pressure chamber distal of the occlusion device and a second pressure chamber proximal to the occlusion device. As shown in FIG. 3C, the exterior surface of the catheter may include pores, slits or slots 323 to provide better dispersion of infusate at the distal end of the catheter and also more precise pressure measurement. Pores, slits, or slots 323 also may be arranged to direct infusate flow pattern, as may be desired for a particular type of diagnosis or therapy. Additional catheter configurations for infusing fluid into a vessel, including mechanisms for centering a distal end of the catheter within a vessel to evenly distribute flow, and to direct infused flow preferentially in antegrade and/or retrograde directions within the vessel, are described with respect to FIGS. 5A-7E of co-pending, commonly assigned U.S. patent application Ser. No. 16/577,962, filed Sep. 20, 2019, and published as U.S. Patent Application Publication No. US2020/0093991 A1, which is incorporated herein by reference.

Figure 4:
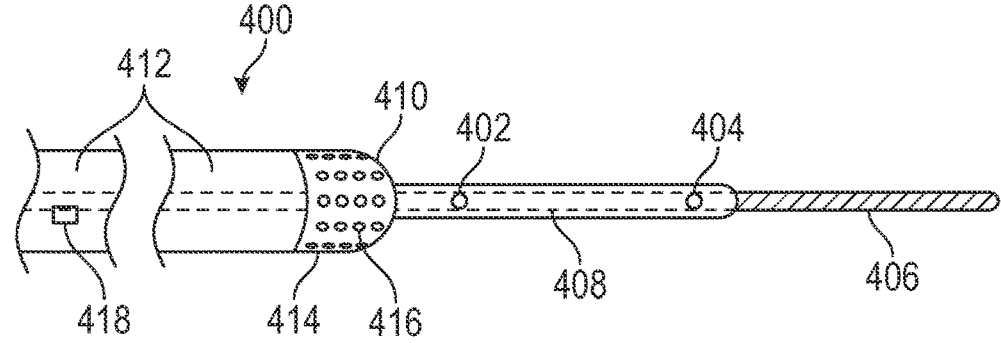
FIG. 4 is a side view of a distal end of a preferred embodiment of a catheter having one or more pressure sensors/transducers.
Figure 5:
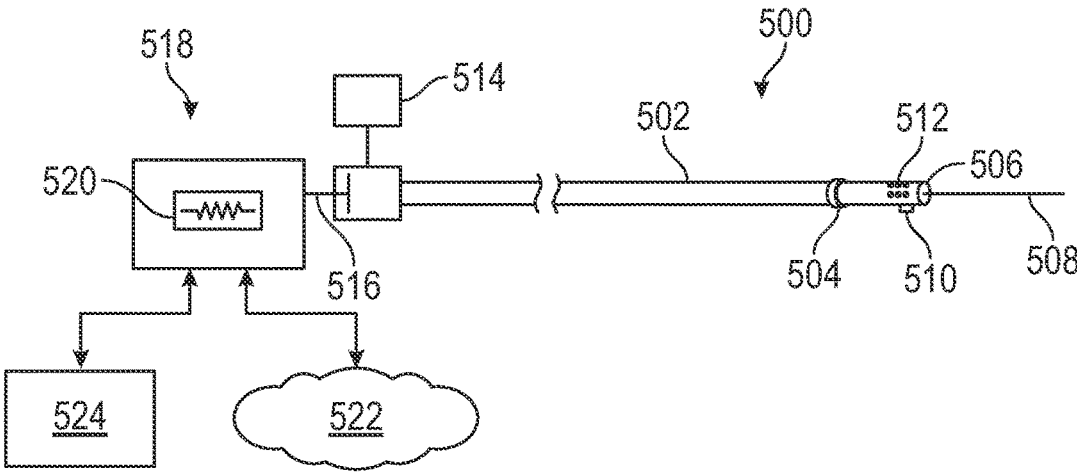
FIG. 5 is a schematic view of a system constructed in accordance with the principles of the present invention.

Referring now to FIGS. 4 and 5, an exemplary embodiment of infusion system constructed in accordance with the present invention, which preferably includes a plurality of pressure sensors. FIG. 4 depicts distal end 400 of a preferred embodiment of catheter that includes distal pressure sensors/transducers 402 and 404. Pressure sensors/transducers 402 and 404 are preferably mounted apart a distance greater than 1 cm longitudinally, and more preferably are spaced apart a distance to permit one sensors to be located on either side of a typical stenosis. Guidewire 406 is disposed in guidewire lumen 408. Distal end 410 of catheter body 412 includes cap 414 containing a plurality of holes 416, in communication with the infusion lumen, through which infusate may be controllably released. Pressure sensor 418 is located proximal to the occlusion system (not shown) of catheter 400. Pressure sensor 418 may be used to obtain pressure measurements upstream of the occlusion device, as discussed in greater detail below.

The pressure sensor configuration shown in FIG. 4 permits measurement of axial intravascular (longitudinal) pressure gradients using pressure sensors/transducers 402 and 404. Longitudinally measured pressure gradients may be used to understand the relationship between vascular/arterial intake size and flow, and thus permit assessment of large vessel resistance in which the catheter lies. For example, fractional flow reserve (FFR) is a parameter that enables assessment of the hemodynamic significance of a coronary artery stenosis, and is typically determined at maximum vasodilation. The two pressure sensor/transducer configuration of FIG. 4 facilitates this measurement without the need for maximum vasodilation. Coronary flow infusion using an infusion pump and pressure measurement allows simple and direct absolute stenosis and hemodynamic quantitation. Other important physiologic parameters similarly may be measured, including coronary flow reserve (CFR), and microvascular resistance as described within herein below. Fluid infusions without oxygen content such an electrolyte solution avoid the need to pharmacologically induce maximum vasodilation using an intravenous or arterial vasodilation agent such as adenosine. This is due to an induced oxygen-poor state with subsequent physiologic vasodilation. In addition, this sensor configuration shown in FIG. 4 allows absolute hydrodynamic resistance to be quantified, which in turn permits fractional flow reserve calculation using mathematical transformation methods.

With respect to FIG. 5, system 500 constructed in accordance with principles of the present invention, as may be embodied in the modular mobile system depicted in FIG. 1 is described. System 500 includes catheter 502 having a focal or general diameter increase, forming a bump 504 and distal end 506. Catheter 502 may be placed advanced into a desired location in a patient's vascular over pressure-sensing guidewire 508. Catheter 502 may be constructed with an internal lumen to accept guidewire 508 in an over-the-wire or rapid exchange modality. Pressure sensor 510 and infusion holes 512 are disposed near distal end 506. Infusate located in reservoir 514 is selectively pumped through catheter 502 via infusate lumen and exits through infusion holes 512 by pump 516. Controller 518, which may include a processor and programmed algorithms, is in communication with pressure sensor 510 and pressure guidewire 508 and is configured to receive pressure readings from those devices.

Controller 518 also is in communication with pump 516 and is configured to control the flow rate of infusate injected via pump 516. Feedback from calculations of resistance parameters, as described below, may be used to adjust the pump, balloon pressure (if present), or operation of other system components to make desired changes in system function and improve diagnostic or therapeutic system function. Controller further includes storage medium 520, which may include RAM, ROM, disk drive, or other known storage media. In some embodiments, storage medium 520 may store algorithms and mathematical calculations disclosed in this application. In some embodiments, storage medium 520 is used to store data that is received from pressure sensor 510 and pressure guide wire 508, as well as to store the resistance parameters, arterial pressures, flow rates, and other values. In some embodiments, storage medium 520 may include a machine-learning algorithm that controls flow rates, performs measurements, and calculates results. In some embodiments, controller 518 may communicate with external wide area networks, such as Internet 522 and/or computing device 524 to communicate data that may be used to refine algorithms in storage medium 520. Controller 518 also may be programmed to access a database of MRI images and parameters derived from those images (such as myocardium at risk data) used to assess microvascular obstruction dysfunction that can be correlated to MVO values computed using the systems and methods of the present invention.

Figure 6:
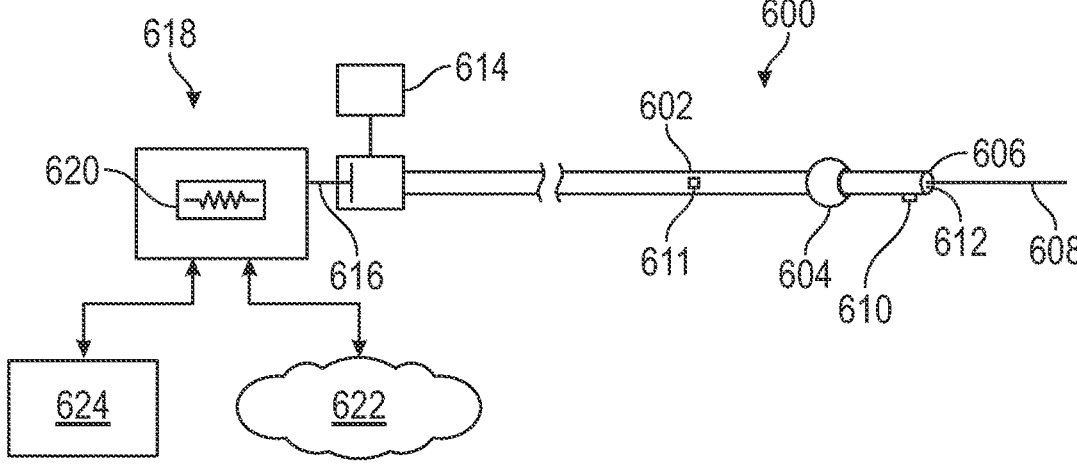
FIG. 6 is a schematic view of a system constructed in accordance with the principles of the present invention.

With respect to FIG. 6, system 600 constructed in accordance with principles of the present invention, as may be embodied in the modular mobile system depicted in FIG. 1 is described. System 600 includes catheter 602 having an occlusion device 604, which may include a balloon near distal end 606. Catheter 602 may be advanced into a desired location in a patient's vascular over pressure-sensing guidewire 608. Catheter 602 may be constructed with an internal lumen to accept guidewire 608 in an over-the-wire or rapid exchange modality. Pressure sensor 610 and distal end 612 of infusion lumen are disposed near distal end 606. Optional pressure sensor 611 may be located proximal to occlusion device 604. Infusate located in reservoir 614 is selectively pumped through catheter 602 via infusate lumen and exits through distal end 612 of infusion lumen by pump 616. Controller 618, which may include a processor and programmed algorithms, is in communication with pressure sensor 610, pressure sensor 611, and pressure guidewire 608 and is configured to receive pressure readings from those devices.

Controller 618 also is in communication with pump 616 and is configured to control the flow rate of infusate injected via pump 616. Feedback from calculations of resistance parameters, as described below, may be used to adjust pump 616, occlusion device 604, or operation of other system components to make desired changes in system function and improve diagnostic or therapeutic system function. Controller further includes storage medium 620, which may include RAM, ROM, disk drive, or other known storage media. In some embodiments, storage medium 620 may store algorithms and mathematical calculations disclosed in this application. In some embodiments, storage medium 620 is used to store data that is received from pressure sensor 610, pressure sensor 611, and pressure guide wire 608, as well as to store the resistance parameters, mean arterial pressures, collateral flow rates, and other calculated values. In some embodiments, storage medium 620 may include a machine-learning algorithm that controls flow rates, performs measurements, and calculates results. In some embodiments, controller 618 may communicate with external wide area networks, such as Internet 622 and/or computing device 624 to communicate data that may be used to refine algorithms in storage medium 620. Controller 618 also may be programmed to access a database of MRI images and parameters derived from those images used to assess microvascular obstruction dysfunction that can be correlated to MVO values computed using the flow analyses methods of the present invention.

In preferred embodiments, the infusion catheters as shown in FIGS. 2-6 may be in communication with a controller that is configured to control a pump, such that the pump provides the infusate via an infusate lumen at a known flow rate or flow rates. Controller is also in communication with pressure sensors, which may be located on a guidewire or elsewhere on the catheter. Controller may also be in communication with other sensors located separate from the catheter, such as known sensors that may be used to measure a patient's systolic and diastolic aortic pressure. As discussed in greater detail below, controller is configured to determine a resistance parameter indicative of a microvascular obstruction. One of skill in the art will appreciate that the disclosed invention will provide apparatus and methods for diagnosing and treating MVO, including treatment by a controlled release of a therapeutic agent at one or more rates determined by the resistance parameter.

In one preferred embodiment, systems 500 or 600 employ an infusion catheter as described with respect to FIG. 4, while in other embodiments the infusion catheters depicted in FIG. 2 or 3, or as described in the above-incorporated U.S. Patent Application Publication No. US2020/0093991 A1 may be employed. Preferably, an infusion catheter suitable for use with the systems 500 or 600 is compatible with a 6F guide sheath, includes a guidewire that accepts a 0.014" pressure guidewire, and is capable of infusing volumetric flow rates in a range of 5 to 50 ml/min. Optionally, the infusion catheter may include a compliant occlusion balloon.

In accordance with the principles of the present invention, the infusion catheter is inserted into an epicardial vessel that supplies blood to a patient's myocardium to assess whether the myocardial vessels distal to or nearby vessels manifest microvascular dysfunction, such as MVO and/or may include dysfunctional vessels responsible for myocardial infarction or ischemia. In a diagnostic mode, the system occludes the blood flow through the vessel and then infuses a fluid into the patient's vessel at a plurality of known flow rates and obtains corresponding pressure measurements distal of the occlusion system. The system also obtains aortic blood pressure measurements, which in some embodiments are obtained with the catheter distal or proximal to the occlusion system. Using the aortic pressure measurements, arterial pressure measurements, and flow rates corresponding to the arterial pressure measurements, a determination of a resistance parameter may be made. Based on the resistance parameter, a diagnosis may be made and a treatment regime may be initiated wherein the flow rates(s) of the therapeutic agent are determined based on the resistance parameter.

Figure 7A:
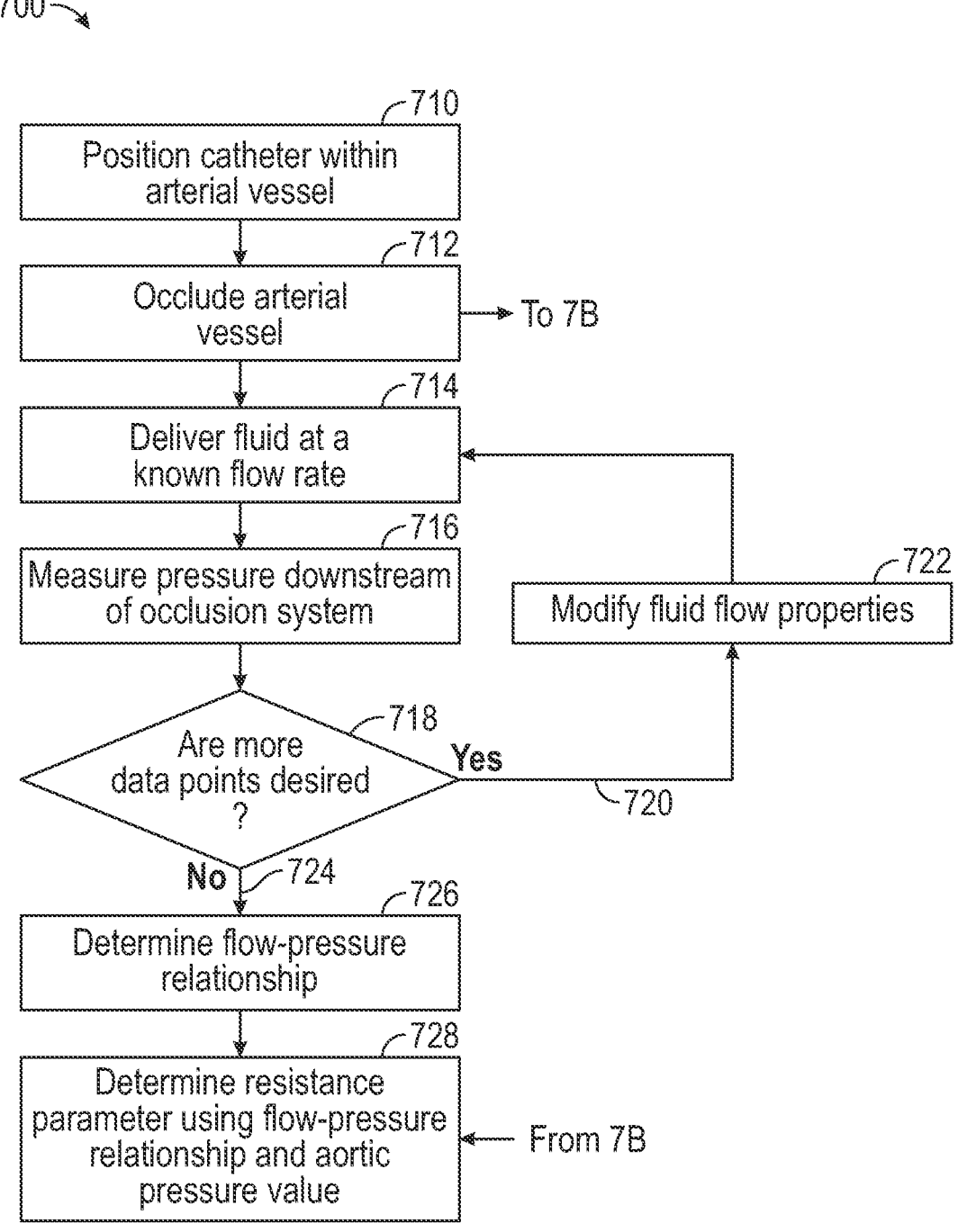

Referring now to FIGS. 7A and 7B, method 700 is described for determining a resistance parameter in accordance with aspects of the present invention utilizing a system such as described in reference to FIGS. 1-6. Beginning with FIG. 7A, at step 710, the distal end of a catheter device is advanced in a patient's arterial vessel to a desired location. The desired location may be selected based on the location of a suspected vascular obstruction, based on a desired location for the placement of a stent, or based on other criteria that will be understood by those of skill in the art.

At step 712, the blood flow in the arterial vessel is occluded by an occluder of the catheter system, which may be achieved, in some embodiments, through the expansion of an occlusion balloon. In other embodiments, the occlusion may be achieved by disrupting the blood flow with a flow of infusate at a sufficient flow rate. Following step 712, method 700 continues as shown in FIG. 7A and FIG. 7B.

Continuing with FIG. 7A, at step 714, fluid is delivered to the arterial vessel at a known flow rate. The fluid is preferably a Newtonian fluid having a substantially linear relationship between pressure and flow rates in some ranges, such as Ringer's lactate, or may be other crystalloid solutions containing beneficial concentrations of sodium, chloride, potassium, glucose, lactate and the like, and may in addition be a drug containing solution. The pressure downstream of the occlusion site is determined at step 716. It will be understood that the pressure measurement is preferably obtained as the fluid is delivered at a known flow rate. In preferred embodiments, the known flow rate and corresponding pressure measurement are stored in a computerized memory, which may be RAM, ROM, flash memory, or other known storage component. Preferably, the known flow rate and pressure measurement are identified as corresponding to one another when stored, such as by a time stamp or other indicia.

At step 718, a decision is made as to whether it is desirable to obtain additional data. In preferred embodiments, a plurality of flow rate and pressure measurement pairs are obtained in order to provide a more accurate analysis. In the event more data is desired, the method proceeds along path 720 to step 722. At step 722, the fluid flow properties are modified, which preferably comprises a different fluid flow rate. The method then returns to step 714, where the fluid is delivered at the modified fluid flow rate. The method continues as before until it reaches step 718. It will be understood that path 720 and ensuing steps may be followed until sufficient pairs of flow rates and corresponding pressure measurements are obtained.

Once sufficient data is obtained, the system proceeds along path 724 to step 726, where a relationship may be determined between the flow rates and corresponding pressures. In preferred embodiments, a linear relationship is determined or assumed based on the data points. Such methods include those described in U.S. Patent Application Pub. No. 2020/0093991, which is incorporated herein by reference.

Notably, following the occlusion of the arterial vessel at step 712, method 700 not only proceeds to step 714, as discussed above, but also proceeds to the steps shown in FIG. 7B. At step 730, an aortic pressure is obtained. In preferred embodiments, the location of the sensor used to obtain the aortic pressure measurements is selected such that a difference between the aortic pressure and the pressure at the downstream pressure sensor is indicative of collateral flow around the occluded vessel.

Following the measurement of aortic pressure, the method proceeds to step 732. If more data is desired, the method proceeds along path 734 back to step 730. In preferred embodiments, the method follows path 734 repeatedly from step 732 until sufficient data points are obtained to calculate a mean value for the aortic pressure. In preferred embodiments, the pressure measurement data is stored and may be time stamped for comparison and possible correlation to the arterial data. Once no further data is desired, the method proceeds from step 732 along path 736 to step 738, where an aortic pressure value is determined. While it is possible that the aortic pressure value may be determined using a single upstream pressure measurement, preferred embodiments of the invention utilize multiple data points and may be used to calculate a mean pressure during a systolic period, a mean pressure during a diastolic period, and/or a mean pressure over the entire heartbeat interval, for example. Method 700 proceeds from step 738 in FIG. 7B to step 728 in FIG. 7A, where the aortic pressure determined at step 738 is used with the flow-pressure relationship determined at step 726 to determine a resistance parameter.

In preferred embodiments, resistance parameter(s) may represent the existence and/or degree of microvascular occlusion in the arterial vessel. A clinician may use the resistance parameter to diagnose the patent by determining the likely presence of an MVO and may determine a course of therapy based on the resistance parameter.

The computerized system may be programmed to indicate a representation of the resistance parameter. In some embodiments, the system may provide this indication as a visual representation on display 102, which may be shown as an image, alphanumeric text, graphs, charts, colored indicators, or the like. Visual indicia may alternatively or in addition comprise lights, such as a warning light. Other outputs that may indicate a representation of the resistance parameter include audio outputs, such as a tone or an alarm if the resistance parameter meets (or does not meet) predetermined criteria, including for example exceeding a predetermined threshold that is selected to correspond to the likely presence of an MVO.

In some embodiments, the representation of the resistance parameter may be compared to other patient data, such as myocardium at risk data obtained via MRI, in order to assist in providing a diagnosis or therapy.

In addition, the computerized system may output the representation of the resistance parameter as computer-readable output, such as, for example, digital data. In preferred embodiments, such digital data may be used by the system to determine a therapeutic treatment. Some embodiments of the invention may provide one or more proposed therapeutic treatment to the clinician for approval, whereas other embodiments may be programmed to automatically proceed to a treatment regime determined based on the resistance parameter.

Notably, in preferred embodiments, the system will disengage the occlusion system during or after the diagnostic phase to allow reperfusion of the blood before reengaging the occlusion system and conducting steps in the therapeutic treatment phase.

Referring now to FIG. 8, method 800 of therapeutic treatment is shown. At step 810, one or more therapeutic flow rates of the therapeutic agent are determined using or based on the resistance parameter. For example, if the resistance parameter is indicative of a minimal MVO, system 100 may determine that therapeutic treatment flow rate of up to 10 ml/min of therapeutic agent is appropriate. As another example, if the resistance parameter indicates a more significant MVO, system 100 may determine that a therapeutic treatment flow rate beginning at 5 ml/min and progressing up to 40 ml/min is appropriate.

At step 820, the therapeutic agent is delivered at a therapeutic flow rate to the patient's arterial vessel via a lumen in the catheter. In preferred embodiments, the therapeutic agent is delivered for a predetermined amount of time, such as a 30-second interval. For example, for a therapeutic cycle of one minute, the therapeutic agent may be delivered for 30 seconds, followed by a 30 second period of dwell time in which no (or minimal) therapeutic agent is delivered.

Step 830 determines whether additional therapy is desired, such as additional therapeutic cycles. If so, path 832 is followed to step 840 where the blood flow may optionally be restored. In preferred embodiments, blood perfusion is temporarily restored following the introduction of a therapeutic agent. For example, for a therapeutic cycle of one minute in which the therapeutic agent is delivered for 30 seconds followed by a 30 second dwell period, the occlusion system may be temporarily disengaged to allow blood perfusion to occur during the dwell time.

At step 850, the therapeutic flow properties optionally may be modified. In preferred embodiments, this modification comprises increasing a flow rate for the therapeutic agent. Proceeding to step 820, the therapeutic agent is delivered at a therapeutic flow rate that may include any modifications indicated by step 850. Method 800 proceeds to step 830 where path 832 may be taken again. One of skill in the art will recognize that as a result, the patient may receive a plurality of infusions of therapeutic agent at different flow rates. In preferred embodiments, the infusion rates are selected such that each infusion rate is equal to or greater than the preceding flow rate.

At step 830, once the desired therapy is delivered, the method proceeds along path 834 to step 860, where the blood perfusion is restored by deflating the occlusion balloon or otherwise discontinuing the occlusion of the blood flow to restore perfusion before reaching end step 870.

Figure 9:
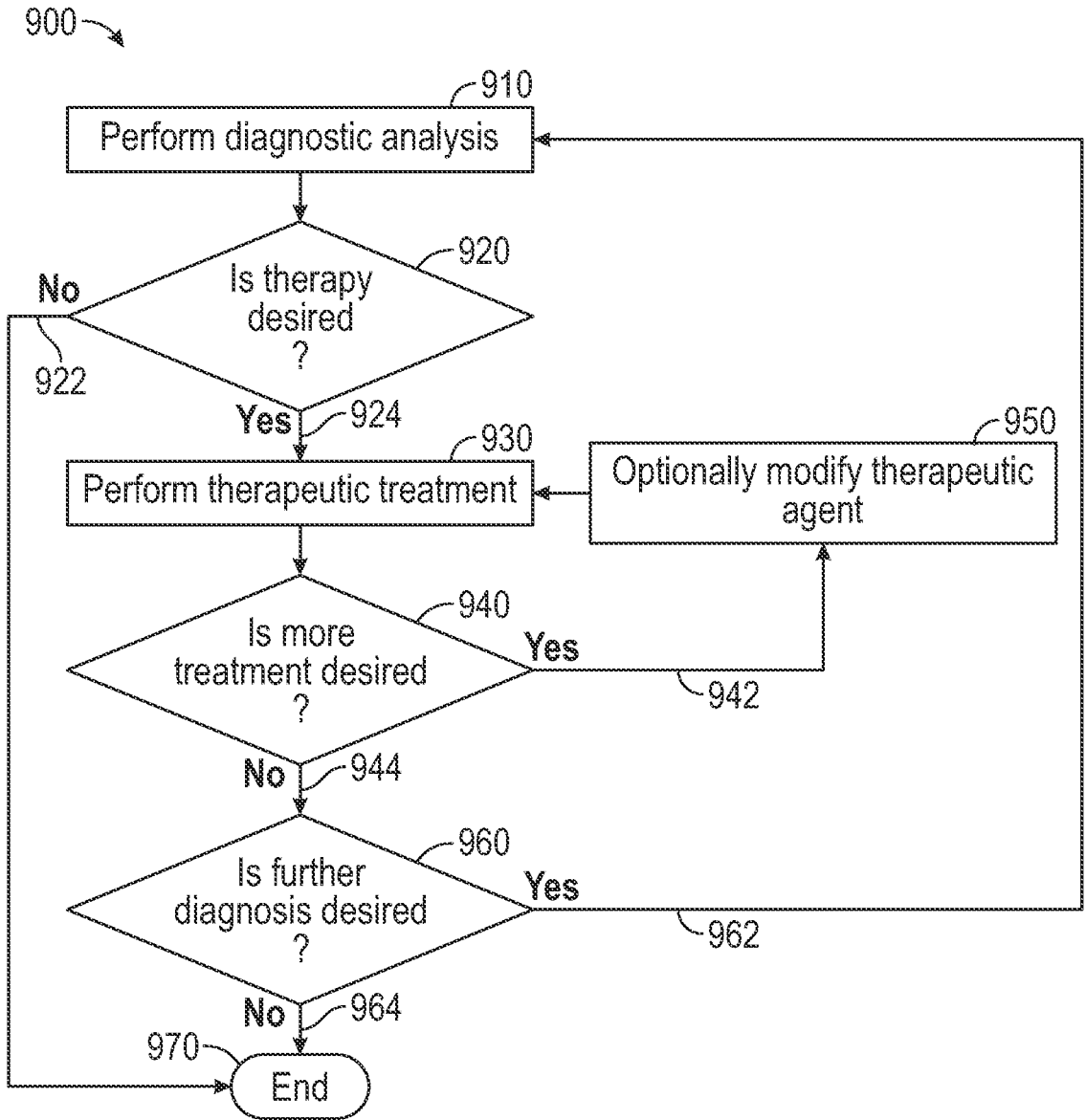
FIG. 9 is a flow chart for providing a plurality of diagnostic analyses and therapeutic treatment in accordance with the principles of the present invention.

Referring now to FIG. 9, method 900 for assessing and treating a patient is shown. At step 910, a diagnosis is performed as presently disclosed, such as in FIGS. 7A and 7B and the associated portions of the specification. As a result of this diagnosis sequence, a resistance parameter is determined. Following the diagnosis step, method 900 advanced to step 920 in which the decision is made whether therapy is desired. For example, the resistance parameter may indicate that little to no MVO is likely present and no therapy is desired. In that scenario, path 922 may be selected which ends the method at step 970.

If, on the other hand, it is decided at step 922 that therapy is desired, the method proceeds along path 924 to step 930, where the therapeutic treatment is conducted. In preferred embodiments, the treatment is conducted as described in regard to FIG. 8. In embodiments in which therapeutic treatment is administered, an interval of blood reperfusion between the diagnostic stage and the therapeutic stage is preferred.

Following the therapeutic treatment stage, the method proceeds to step 940 at which a decision is made whether to perform additional treatment. If so, the method proceeds along path 942 to step 950 in which the therapeutic agent may be modified. For example, a first therapeutic agent may be discontinued and replaced with a different second therapeutic agent. The method them returns to step 930 and treatment is resumed. Once the process returns to step 940, it may continue to cycle through any other desired modifications of the therapeutic agent until the no more treatment is desired at step 940. The process then follows path 944 to step 960 to determine whether further diagnosis is desired. If so, the method returns to step 910 and resumes as discussed above. And if not, the method ends at step 970. In some preferred embodiments, it is desirable to conduct a final diagnostic analysis following the final treatment step to assess the patient's condition at the conclusion of therapy. In such embodiments, the method may proceed from step 940 to step 960, then along path 962 to step 910, then step 920 and then along path 922 to step 970.

Systems and methods of the present invention may be further explained using the following examples.

Figure 10:
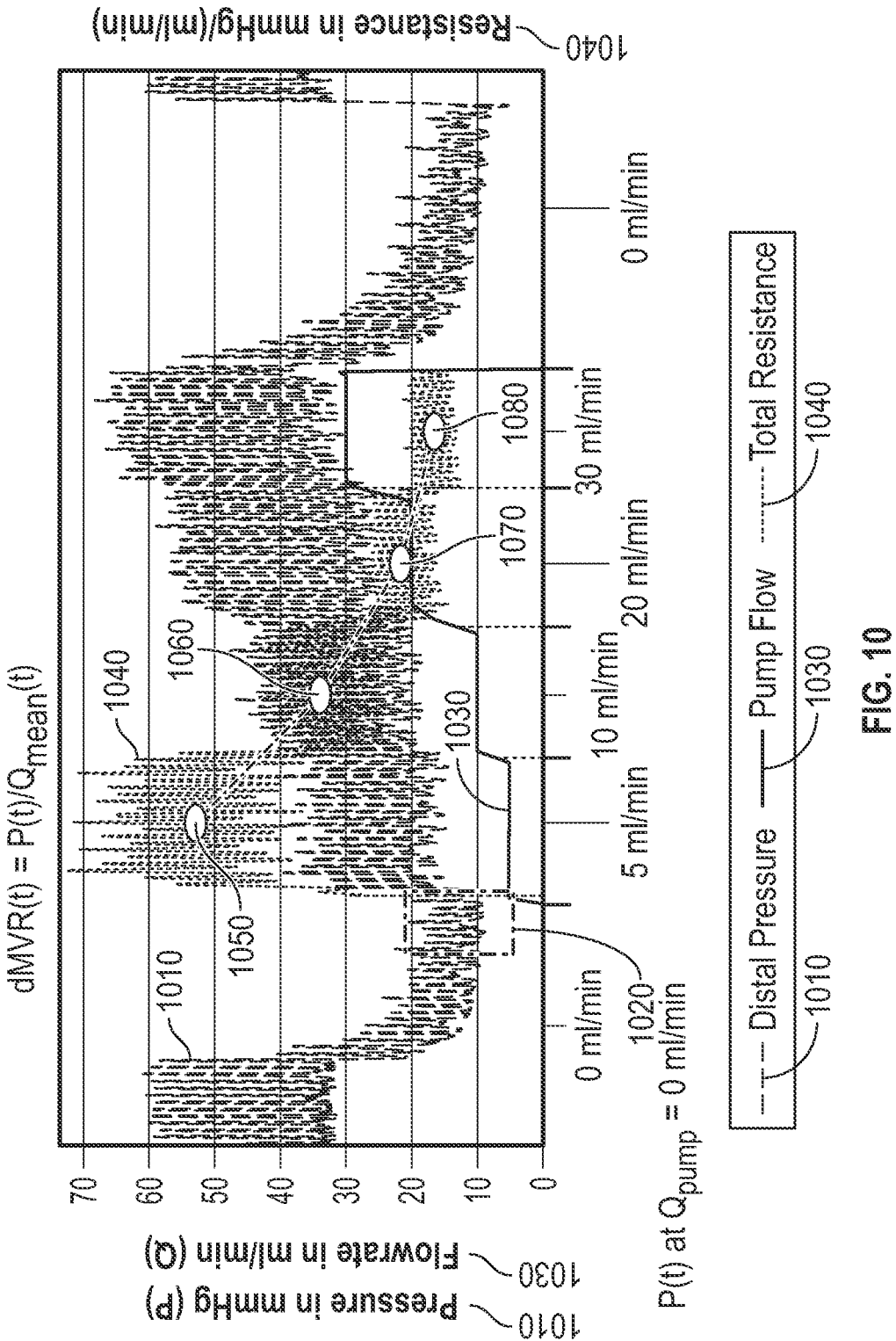
FIG. 10 is a plot of distal pressure, pump flow, and resistance in an example of a portion of a diagnostic sequence in accordance with the principles of the present invention.

Referring now to FIG. 10, an example of a portion of a diagnostic sequence is described. A balloon catheter of system 100 in accordance with the present invention is placed within a patient's arterial vessel. A pressure sensor distal to the occlusion device is used to obtain pressure measurements within the vessel, and pressure measurements obtained by pressure measurement system 104 may be processed by controller 101 for viewing in, for example, a graphical format on display 102. A representation of the pressure measurements in this example is shown as line 1010 in FIG. 10. It will be recognized that the distal pressure increases and decreases in rapid succession, which corresponds to the systolic and diastolic pressures. At the beginning of the sequence described in FIG. 10, the systolic pressure measurements are nearly 60 mmHg, whereas the diastolic pressure measurements are slightly more than 30 mmHg, as shown on line 1010. After the occlusion balloon is used to obstruct antegrade artery flow, the blood pressure drops and a "waterfall pressure" (aka Coronary Artery Wedge Pressure) is measured. The coronary wedge pressure, denoted $P_{cwp}$, may be calculated as the mean pressure at an interval after the occlusion device obstructs the vessel and prior to the infusion of a fluid, e.g., as $Q_{pump}=0$ ml/min. In FIG. 10, element 1020 denotes the interval and distal pressure measurements considered for the determination of an exemplar coronary wedge pressure.

Infusion pump 103 begins to infuse a fluid, such as Ringer's lactate, at a rate of 5 ml/minute, as depicted by line 1030. As the fluid is infused, it will be observed that pressure measurements 1010 increase. A relationship between the distal pressure, Pd and the infusate flow rate may be determined using the equation: resistance=(distal pressure)/(infusate flow rate), where in the present example distal pressure is measured in mmHg, infusate flow rate is measured in ml/min, and resistance is measured in mmHg/(ml/min). A representation of the resistance is disclosed by line 1040 in FIG. 10.

It is observed that as the infusate flow is increased in a relatively stepwise fashion, shown in line 1030, the distal pressure increases, shown in line 1010, whereas the resistance decreases, shown in line 1040. Once the infusion is discontinued, which occurs after the 30 ml/min infusion rate, the distal pressure measurements again decrease to a coronary wedge pressure until the occlusion balloon is deflated allowing blood perfusion to resume.

The data collected by pressure measurement system 104 may be processed by controller 101 to determine one or more mean distal pressure ($P_d$) values. In some preferred embodiments, as described in reference to FIG. 10, a mean distal pressure is determined over a plurality of time periods. Here, the infusate delivery included several intervals in which the infusion rate was constant, and the mean distal pressure was determined as the average pressure over each of those intervals. These mean distal pressure determinations may then be divided by the corresponding infusate flow rate to yield mean dynamic Microvascular Resistance (dMVR) values, wherein mean dMVR=$(P_d)/(Q_{pump})$ at each flow rate.

For example, element 1050 represents a mean dMVR over an interval when $Q_{pump}$ was 5 ml/min, element 1060 represents a mean dMVR over an interval when $Q_{pump}$ was 10 ml/min, element 1070 represents a mean dMVR over an interval when $Q_{pump}$ was 20 ml/min, and element 1080 represents a mean dMVR over an interval when $Q_{pump}$ was 30 ml/min.

Additionally, a mean coronary microvascular resistance for each of the intervals may then be calculated as: mean coronary microvascular resistance=$(P_d-P_{cwp})/Q_{pump}$.

Figures 11A, 11B:
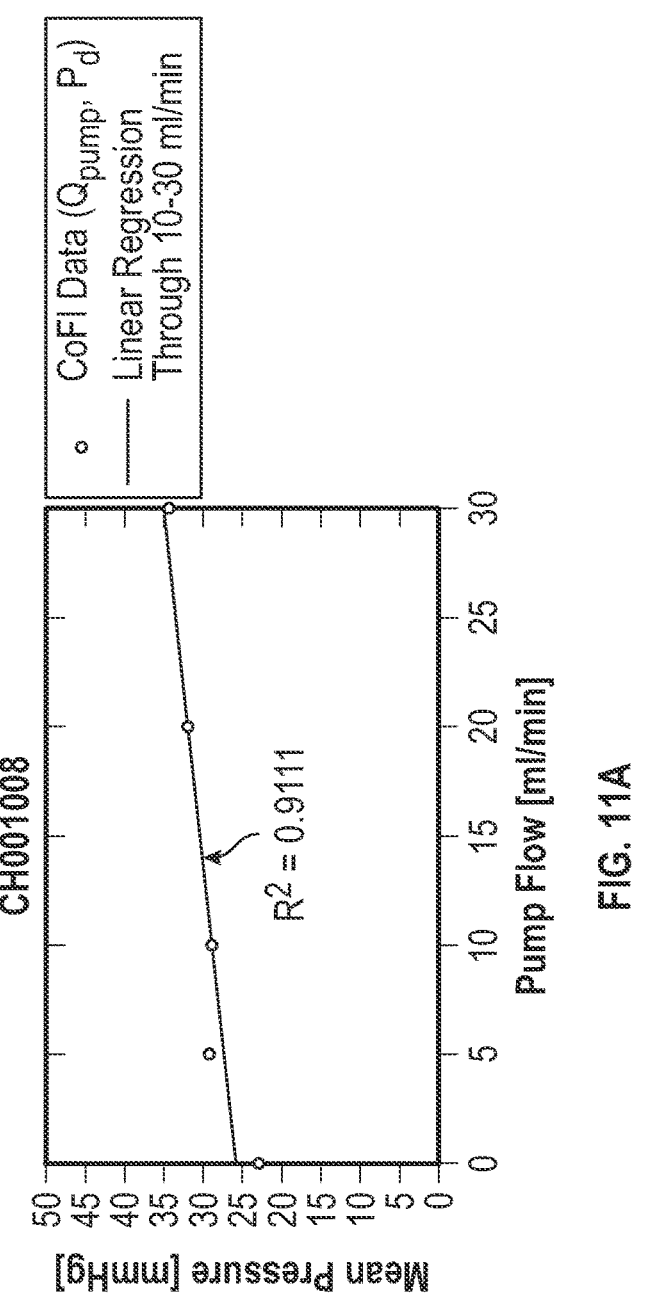
FIGS. 11A and 11B are a graph of pump flow, pressure, and their linear relationship, as well as the corresponding data in accordance with the principles of the present invention.

Data acquired during a diagnostic sequence is used to determine a relationship between the infusion rates ($Q_{pump}$) and the distal pressures. An example of such a relationship is described in relation to FIGS. 11A and 11B, which includes data obtained from a representative human STEMI patient. For example, for each of several infusate flow rates of 0 ml/min, 5 ml/min, 10 ml/min, 20 ml/min, and 30 ml/min, a corresponding mean distal pressure was determined, which are shown in FIG. 11B. The corresponding pressure and flow rate pairs are plotted in FIG. 11A with points denoted as CoFI data ($Q_{pump}$, $P_d$). Linear regression techniques were utilized to determine a linear relationship between the data points. It will be appreciated that not all the points need be used. In this example the data points corresponding to 10 ml/min, 20 ml/min, and 30 ml/min were used, as it has been determined that $P_d$ at $Q_{pump}$=5 ml/min may be omitted, because such low flow rates likely alter the distal microvascular resistance due to low intravascular pressures associated with these low flow rates.

In addition, and consistent with previous observations the inventors have made, the $Q_{pump}$ and $P_d$ coordinate pairs in the example if FIGS. 11A and 11B exhibit a linear dependence at flow rates above 5 ml/min. This characteristic dependence of pressure and flow suggests a steep decrease of mean microvascular resistance for increasing infusion rates and subsequent convergence to a constant resistance value given by the slope of the regression line (asymptotic coronary microvascular resistance). This behavior is also illustrated in FIG. 10, where the dynamic Microvascular Resistance (dMVR) indicated by line 1040 decreases notably during the first infusion steps and approaches a constant mean value for further increases in pump infusion rate.

Characteristics of the line in FIG. 11A found by linear regression analysis are presented in FIG. 11B, including the slope, Y-axis intercept, and $R^2$ values. It will be appreciated that other (e.g. non-linear) relationships between the fluid flow rates and the corresponding distal pressures may be found and that those relationships may include different characteristics.

Figure 12:
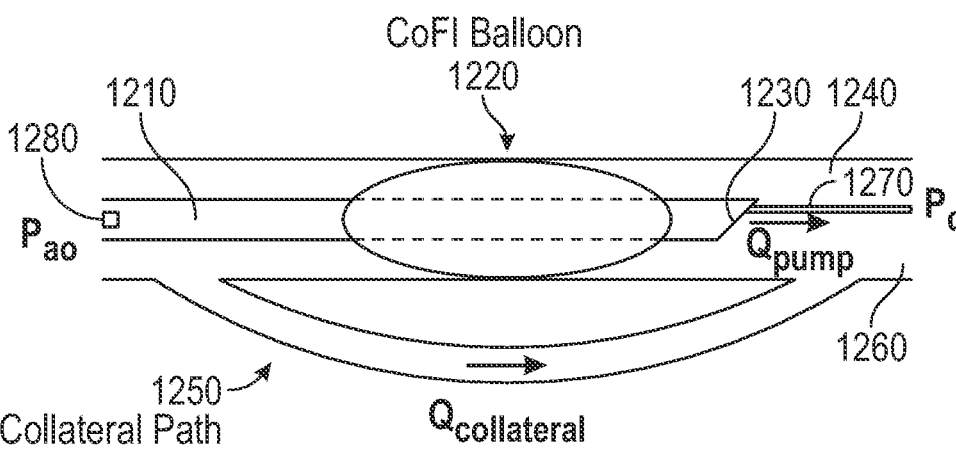
FIG. 12 is a representation the distal end of a catheter in a vessel subject to collateral flow in accordance with the principles of the present invention.
Figure 13:
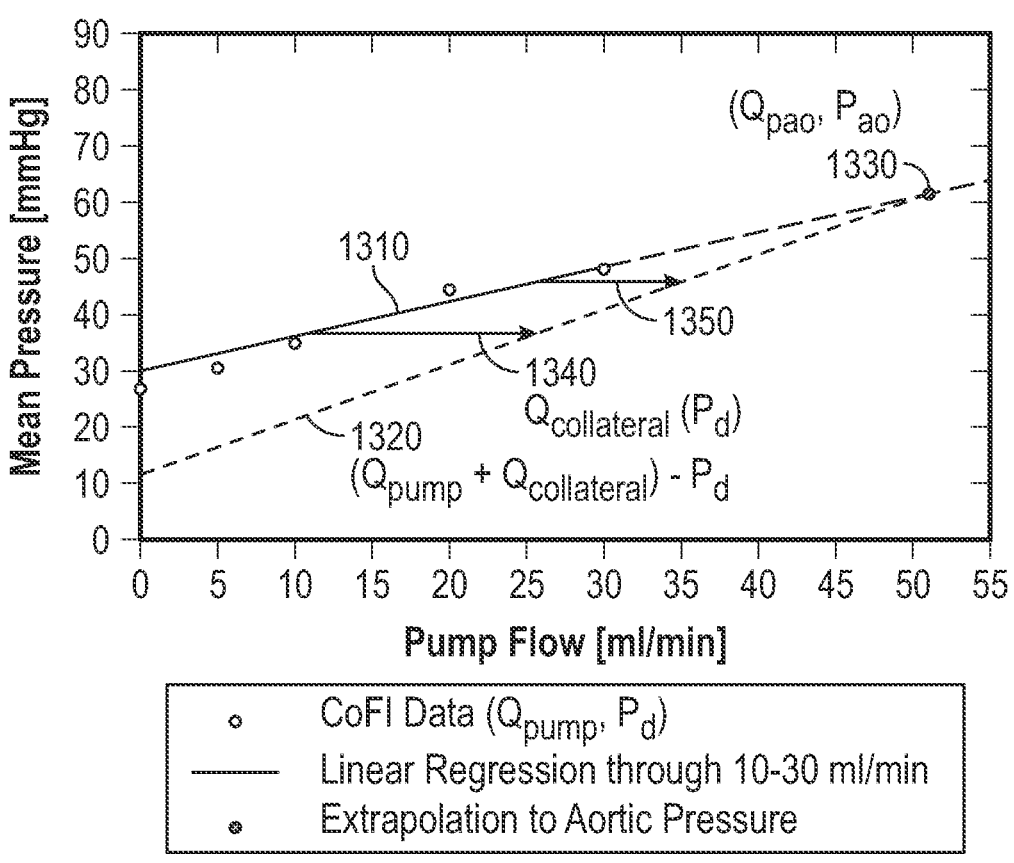
FIG. 13 is a graph of pump flow, pressure, and their linear relationships in accordance with the principles of the present invention.

As described in regard to FIGS. 12 and 13, in accordance with the present invention, the presence of collateral flow may be recognized and accounted for. FIG. 12 depicts distal portion of catheter system 1210 of infusion system 100, including occlusion balloon 1220, and distal end of infusate lumen 1230. Fluid, therapeutic agent, or other infusate may be delivered to vessel 1240 by pump 103 via distal end of infusate lumen 1230 at a flow rate denoted as $Q_{pump}$. Pressure sensing guidewire 1270 is configured to obtain pressure measurements by point 1260, distal to balloon 1220. Optionally, device may include proximal pressure sensor 1280, which is configured to obtain pressure measurements proximal of balloon 1220. It will be understood that in some embodiments, distal portion of catheter system 1210 may include a stent (not shown) that may be deployed via inflation of occlusion balloon 1220 or other balloon (not shown).

As described in FIG. 12, collateral path 1250 exists that is in fluid communication with vessel 1240 distal and proximal of the occlusion device, balloon 1220. It will be appreciated that some amount of blood flow may occur through collateral path at a flow rate that may be represented as $Q_{collateral}$. Accordingly, the flow rate by point 1260 distal to collateral path 1250 may be found as the combination of the flow rates through the infusion lumen and the collateral path, which can be expressed as $(Q_{pump}+Q_{collateral})$.

It will be appreciated by one of skill in the art that collateral flow is driven by a pressure differential. When the pressure at the distal end of a collateral pathway is equal to the pressure at the proximal end of the collateral pathway, the impetus for fluid flow is absent (driving pressure gradient is zero) and collateral flow ceases. In considering the collateral flow, it is useful to consider the mean aortic pressure ($P_{ao}$), which may remain essentially unchanged over an interval during a diagnostic sequence. As one of skill in the art will recognize, there are a variety of methods to determine mean aortic pressure. For example, the mean aortic pressure may be determined as an average of systolic pressures and diastolic pressures, or as a weighted comparison of systolic pressures and diastolic pressures (such as by considering two-thirds of the diastolic pressure and one-third of the systolic pressure), or as determined by other known methods.

When collateral flow is present, the asymptotic coronary microvascular resistance previously determined by the relationship between $Q_{pump}$ and $P_d$ may be further refined to account for $Q_{collateral}$. By way of example, FIG. 13 depicts a graph in which a number of infusion flow rates and corresponding distal pressure data point pairs have been graphed for flow rates of 5, 10, 20 and 30 ml/min, identified as ($Q_{pump}$, $P_d$). Similar to FIG. 11, linear regression was used to determine a linear relationship between the infusion flows and the distal pressure, shown by line 1310. Line 1310 may be extended to point 1330, corresponds to the data point ($Q_{pao}$, $P_{ao}$), at which the collateral flow rate longer contributes to the overall flow rate. To account for the collateral flow, however, the relationship between ($Q_{pump}+Q_{collateral}$) and $P_d$ is considered, which is depicted as line 1320. It will be appreciated that the effects of the collateral flow rate on the overall flow rate decreases as the infusion flow rate increases to a rate at which $P_d$ equals $P_{ao}$, as indicated by line 1340 and line 1350. At point 1330, it may be assumed that $Q_{pao}$ is $Q_{pump}$. Line 1320 may be extended to point 1330, ($Q_{pao}$, $P_{ao}$), at which the collateral flow rate may be assumed to no longer contribute to the overall flow rate.

Collateral flow is driven by the low pressure distal to balloon 1220 while balloon 1220 is occluding vessel 1240.

As demonstrated in FIG. 12, collateral flow ($Q_{collateral}$) corresponds to the difference between mean aortic pressure ($P_{ao}$) and the distal pressure ($P_d$) during the diagnostic sequence. As $P_d$ varies during the diagnostic sequence and $P_{ao}$ remains constant, collateral flow is relatively large at low $Q_{pump}$ values and decreases for increasing $Q_{pump}$ flow rates (and increasing distal pressure $P_d$ measures). In reference to FIGS. 12 and 13, a more clinically significant relationship may be found between $P_d$ and the total flow ($Q_{pump}+Q_{collateral}$) at point 1260 than exists between $P_d$ and $Q_{pump}$ at point 1260. It is therefore desirable to benefit from the relationship indicated by line 1320 in FIG. 13. One of skill in the art will recognize that, in comparison to line 1320, line 1310 overestimates the pressure response, particularly in relation to low $Q_{pump}$ infusion rates. Thus, asymptotic coronary resistance found using the slope of line 1310 is underestimated as compared to that of line 1320. To correct for this effect, line 1310 is extrapolated to a theoretical point of collateral flow suppression, where the pressure gradient across balloon 1220 is negligible or nonexistent (that is, $P_d$ is the same, or nearly the same, as $P_{ao}$, which occurs at point 1330). A resistance parameter of asymptotic coronary microvascular resistance may then be computed as $P_{ao}/Q_{pao}$. The resistance parameter of asymptotic coronary microvascular resistance assumes that the resistance is converged at point 1330 and that the effect of ignoring the zero-flow pressure is small, because $P_{ao}$ is significantly greater than $P_{cwp}$.

There are various methods to determine $P_{ao}$. In accordance with some aspects of the invention, $P_{ao}$ may be determined as the average pressure proximal to the occlusion device over a time frame at the beginning of the diagnostic sequence, when balloon 1220 is deflated. In the example of FIG. 12, such measurements of the aortic pressure may be obtained with pressure sensor 1280. $Q_{pao}$ may then be computed using the equation $Q_{pao}=(P_{ao}-b)/M$, where m is the slope and b is the Y-axis intercept of the line found by linear regression through the $Q_{pump}$ and $P_d$ data point pairs when determining the relationship between those data point pairs. For FIG. 13, a linear relationship was found for $Q_{pump}=10, 20, 30$ ml/min, respectively. One of skill in the art will understand that once a linear relationship is found, the slope and Y-axis intercept of the line may be readily determined, such as indicated in FIGS. 11A and 11B.

In other embodiments, $P_{ao}$ may be determined using sensors that are in communication with system 100, but are not located on the catheter body.

It will be appreciated that preferred embodiments of the present invention rely on empirical solutions to determine $Q_{pao}$. For example, $P_{ao}$ may be determined by one of the embodiments described herein or as known to those of skill in the art. Then, during a diagnostic sequence, $Q_{pump}$ may be increased until the measured value of $P_d$ is at or near the determined value of $P_{ao}$. Once that pressure is reached, collateral flow may be assumed to be negligible or nonexistent and $Q_{pao}$ may be assumed to be $Q_{pump}$, which may be readily obtained using pump 103.

Figure 14:
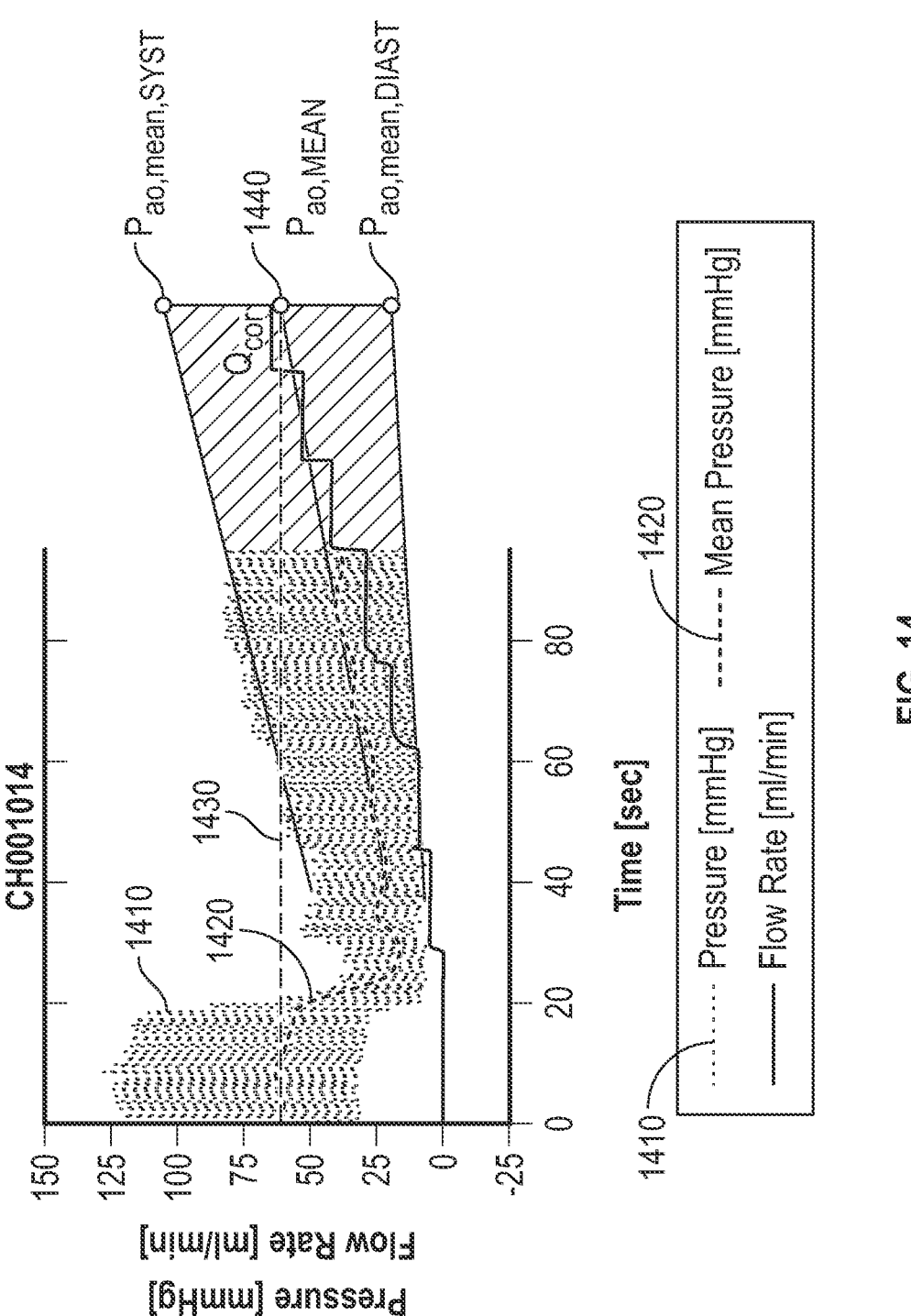
FIG. 14 is a plot of distal pressure, mean pressure, and flow rates in accordance with the principles of the present invention.

Turning now to FIG. 14, yet another example of the determination of $P_{ao}$ is described. FIG. 14 describes distal pressure measurements ($P_d$), line 1410, such as may be obtained by pressure sensing guidewire 1270 at point 1260 in FIG. 12. It will be appreciated that when $Q_{pump}$ is zero and prior to the occlusion of vessel 1240, there should be negligible difference between $P_d$ and $P_{ao}$. Accordingly, a clinician may obtain pressure measurements distal to the occlusion device prior to the occlusion of the vessel to obtain a mean pressure that can represent the mean aortic pressure, $P_{ao}$. In reference to FIG. 14, a mean pressure 1420 may be determined distal to the occlusion device, such as by pressure sensing guidewire 1270 at point 1260 in FIG. 12. The mean pressure taken during the first 10 seconds as represented on the x-axis of FIG. 14 may represent $P_{ao}$, indicated as dotted line 1430 in FIG. 14. Then, the fluid may be delivered using system 100 as described above until the measured value of $P_d$ reaches the previously-determined value of $P_{ao}$. At that point, $Q_{pao}$ may be assumed to equal the rate at which system is delivering the fluid, $Q_{pump}$.

In the examples described with respect to FIGS. 12, 13, and 14, it is shown that a relationship may be found between a plurality of flow rates provided by infusion pump 103 of system 100 on one hand, and arterial pressures corresponding to the plurality of flow rates on the other hand. An example of this relationship is demonstrated by line 1310, determined by linear regression of the data point pairs. It is also shown that an aortic pressure may be found, such as a mean aortic pressure considered over an interval during a diagnostic sequence. The aortic pressure may be used to determine an infusion rate at which $Q_{pump}$ is assumed to be $Q_{pao}$. The values of $Q_{pao}$ and $P_{ao}$ may be used to be determine a resistance parameter found by the relationship a $P_{ao}/Q_{pao}$.

In some embodiments of the invention, system 100 need not determine a relationship between $Q_{pump}$ and $P_d$ during the diagnostic sequence. Rather, $P_{ao}$ may be obtained, as described herein, and then $Q_{pump}$ may by increased in a series of increments, such as in a stepwise fashion, until the measured value of $P_d$ approximates $P_{ao}$. At that point, $Q_{pao}$ is assumed to be the $Q_{pump}$ corresponding to $P_d$.

A resistance parameter may be found using the values of $P_{ao}$ and $Q_{pao}$ obtained during a diagnostic sequence, wherein the resistance parameter is found by dividing $P_{ao}$ by $Q_{pao}$. The inventors have discovered that such a resistance parameter is useful in predicting the presence of MVO.

Figure 15:
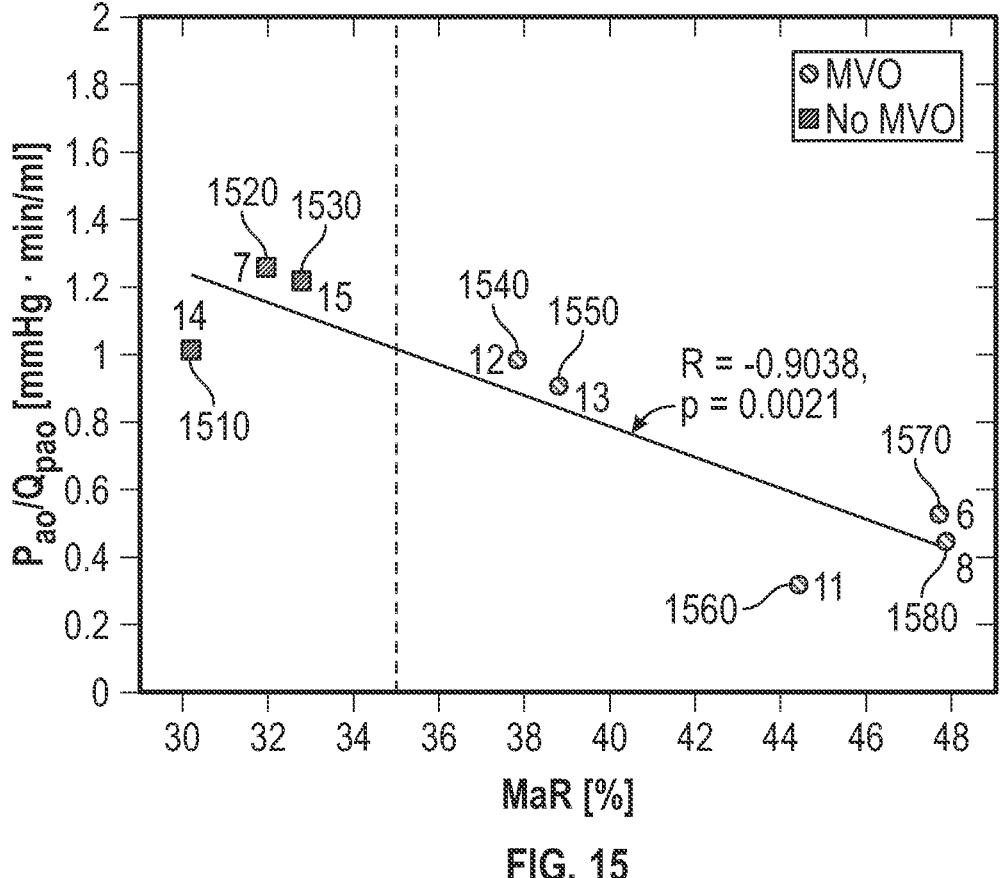
FIG. 15 is a graph of resistance parameters and myocardium at risk values for patients that may be used for diagnostic and/or therapeutic purposes in accordance with the principles of the present invention.

Referring to FIG. 15, a chart depicting a collection of resistance parameters (found by dividing $P_{ao}$ by $Q_{pao}$) is compared to the patient's corresponding myocardium at risk (MaR) as a percentage of the left ventricle mass. It is shown through regression analysis that a correlation exists between the resistance parameters and the MaR that may be used to indicate the presence or absence of MVO. For example, data points 1510, 1520, and 1530 were associated with patients having no MVO, whereas data points 1540, 1550, 1560, 1570, and 1580 were associated with patients having MVO. One of skill in the art will understand that resistance parameters found in the diagnostic sequence of the present invention may be utilized with MaR data (obtained via MRI) to predict the presence of MVO and to determine whether therapeutic treatment is suggested.

It is to be understood that the implementations described herein are illustrative and that the scope of the present invention is not limited to those specific embodiments; many variations, modifications, additions, and improvements are possible. For example, functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method of determining a vascular physiological parameter for a patient, the method comprising:
   advancing a catheter having a lumen and a distal end and a first pressure sensor into an arterial vessel of the patient, the arterial vessel having blood flow;

delivering fluid at a plurality of flow rates over a time period through the lumen into the arterial vessel;

measuring a plurality of arterial pressures in the arterial vessel over the time period via the pressure sensor, the plurality of pressures corresponding to the plurality of flow rates;

determining a measure of aortic pressure of the patient, the measure of aortic pressure representative of an aortic pressure during the time period;

determining a resistance parameter using the measure of aortic pressure, a relationship between the plurality of flow rates over the time period and the plurality of arterial pressures over the time period, and a flow rate at which a corresponding pressure corresponds to the measure of aortic pressure; and generating a representation of the resistance parameter.

2. The method of claim 1, wherein the step of generating the representation of the resistance parameter comprises displaying a visual indicator.

3. The method of claim 1, further comprising:

delivering a therapeutic agent at a plurality of therapeutic flow rates via the catheter into the arterial vessel.

4. The method of claim 3, wherein the step of generating the representation of the resistance parameter comprises generating an electronic output.

5. The method of claim 4, wherein the plurality of therapeutic flow rates are determined using the electronic output.

6. The method of claim 5, further comprising:

initiating a first occlusion of the blood flow prior to the step of delivering fluid at the plurality of flow rates.

7. The method of claim 6, further comprising:

discontinuing the first occlusion of the blood flow subsequent to the step of delivering fluid at the plurality of flow rates.

8. The method of claim 7, further comprising:

initiating a second occlusion of the blood flow, wherein the step of initiating the second occlusion of the blood flow occurs subsequent to the step of discontinuing the first occlusion of the blood flow and prior to the step of delivering the therapeutic agent.

9. A system for diagnosing or treating a patient having an arterial vessel, the system comprising:

a catheter system having an occlusion device, a pressure sensor disposable distal to the occlusion device, and a lumen sized to deliver fluid therethrough to the arterial vessel distal of the occlusion device, the occlusion device being configured to occlude blood flow through the arterial vessel by initiating an occlusion of blood flow and subsequently discontinuing the occlusion; and a computerized infusion system configured to be coupled to the catheter system and to:

cause the fluid to be infused at a plurality of flow rates via the lumen and subsequent to the occlusion device initiating the occlusion and prior to the occlusion device discontinuing the occlusion;

communicate with the first pressure sensor to receive a plurality of pressure measurements over a time period, the plurality of pressure measurements corresponding to the plurality of flow rates over the time period;

calculate a resistance parameter using an aortic pressure measurement representative of an aortic pressure during the time period, the plurality of pressure measurements over the time period, and the plurality of flow rates over the time period, and a flow rate at which a corresponding pressure corresponds to the aortic pressure measurement; and generate a representation of the resistance parameter.

10. The system of claim 9, wherein the computerized infusion system is further configured to cause a therapeutic agent to be infused at a plurality of therapeutic infusion rates.

11. The system of claim 10, wherein the representation of the resistance parameter comprises an electronic output.

12. The system of claim 11, wherein the plurality of therapeutic infusion rates are determined based on the electronic output.

13. The system of claim 9, wherein the occlusion device may be activated to occlude the arterial vessel, and wherein the computerized infusion system is further configured to selectively activate the occlusion device.

14. The system of claim 10, wherein the representation of the resistance parameter comprises a visual image.

15. The system of claim 14, wherein the computerized infusion system is coupled to a display device, the display device configured to display the visual image.

16. A system for diagnosing or treating a patient having an arterial vessel, the system comprising:

a catheter system having a catheter body carrying an occluder, a first pressure sensor located distal to the occluder, a second pressure sensor (1) located proximal to the occluder and remote from (a) the first pressure sensor and (b) the catheter body, and (2) configured to obtain aortic pressure measurements, and a lumen sized to deliver fluid to the arterial vessel distal of the occluder; and a computerized infusion system configured to be coupled to the catheter system and to:

cause the fluid to be infused at a plurality of flow rates;

communicate with the first pressure sensor to receive a plurality of downstream pressure measurements over a time period, the plurality of downstream pressure measurements corresponding to the plurality of flow rates over the time period;

communicate with the second pressure sensor to receive aortic pressure measurements, the aortic pressure measurements representative of an aortic pressure during the time period; and calculate a resistance parameter based on an aortic pressure measurement measured by the second sensor, the plurality of downstream pressure measurements over the time period, and the plurality of flow rates over the time period.

17. The system of claim 16, wherein the computerized infusion system is further configured to infuse a therapeutic agent at a first infusion rate determined by the resistance parameter.

18. The system of claim 17, wherein the computerized infusion system is further configured to cause the fluid to be infused for a predetermined diagnostic interval, to infuse the therapeutic agent at the first infusion rate for a first predetermined treatment interval, and to infuse the therapeutic agent at a second infusion rate for a second predetermined treatment interval, the second infusion rate being based on the resistance parameter.

19. The system of claim 16, wherein the computerized infusion system is further configured to operate the occluder.

20. The system of claim 16, wherein the computerized infusion system is coupled to a display device, the display device configured to display an indication of the resistance parameter.

21. The method of claim 1, further comprising:
initiating a first occlusion of the blood flow prior to the step of delivering fluid at the plurality of flow rates,
the step of determining the measure of aortic pressure includes determining the measure of aortic pressure prior to initiating the first occlusion.

22. The method of claim 21, wherein the step of determining the measure of aortic pressure includes determining the measure of aortic pressure using the pressure sensor.

23. The method of claim 22, wherein the pressure sensor is a pressure sensing guidewire, a distal end of the pressure sensing guidewire being disposed distal to the catheter during the step of determining the measure of aortic pressure.

24. The method of claim 21, wherein the pressure sensor is a first pressure sensor,
the step of determining the measure of aortic pressure includes determining the measure of aortic pressure of the patient via a second pressure sensor remote from the first pressure sensor and separate from the catheter.

25. The method of claim 24, wherein the step of determining the measure of aortic pressure via the second pressure sensor occurs during the time period.

26. The method of claim 1, further comprising:
performing regression analysis using the plurality of flow rates and the plurality of pressures corresponding to the plurality of flow rates to determine the flow rate at which the corresponding pressure corresponds to the measure of aortic pressure.

27. The method of claim 1, wherein the resistance parameter is representative of microvascular dysfunction.

28. The method of claim 1, wherein delivering fluid at the flow rate at which the corresponding pressure corresponds to the measure of aortic pressure renders negligible any collateral flow associated with the arterial vessel.

29. The method of claim 1, wherein the flow rate at which the corresponding pressure corresponds to the measure of aortic pressure is calculated based on the relationship between the plurality of flow rates over the time period and the plurality of arterial pressures over the time period.

30. The method of claim 1, wherein the plurality of flow rates over the time period does not include the flow rate at which the corresponding pressure corresponds to the measure of aortic pressure.

31. The system of claim 9, wherein the computerized infusion system is configured to cause the fluid to be infused at the plurality of flow rates subsequent to the occlusion device initiating the occlusion and prior to the occlusion device discontinuing the occlusion.

32. The system of claim 9, wherein the pressure sensor is a first pressure sensor, the catheter system further including a second pressure sensor located proximal to the occlusion device and configured to obtain the aortic pressure measurement representative of the aortic pressure during the time period.

33. The system of claim 31, wherein the computerized infusion system is configured to: (1) obtain the aortic pressure measurement prior to the occlusion device initiating the occlusion, and (2) receive the plurality of pressure measurements subsequent to the occlusion device initiating the occlusion and prior to the occlusion device discontinuing the occlusion.

34. The system of claim 9, wherein the pressure sensor is disposable distal to the lumen.

35. The system of claim 9, wherein the pressure sensor is a pressure sensing guidewire.

36. The system of claim 16, wherein the computerized infusion system is configured to calculate the resistance parameter based on a flow rate at which a corresponding pressure corresponds to the aortic pressure measurement.

37. The system of claim 36, wherein the flow rate is greater than all of the plurality of flow rates, the computerized infusion system configured to calculate the flow rate using regression analysis.

* * * * *